(12) United States Patent
Ebensen et al.

(10) Patent No.: US 8,211,463 B2
(45) Date of Patent: Jul. 3, 2012

(54) USE OF GLYCOLIPIDS AS ADJUVANTS

(75) Inventors: Thomas Ebensen, Hannover (DE);
Michael Morr, Wolfenbuettel (DE);
Carlos Guzman, Wolfenbuettel (DE);
Goetz Milkereit, Hamburg (DE)

(73) Assignee: Helmholtz-Zentrum Fuer Infektionsforschung GmbH, Braunschweig (DE)

( * ) Notice: Subject to any disclaimer, the term of this patent is extended or adjusted under 35 U.S.C. 154(b) by 641 days.

(21) Appl. No.: 12/440,315

(22) PCT Filed: Sep. 6, 2007

(86) PCT No.: PCT/EP2007/007794
§ 371 (c)(1),
(2), (4) Date: Mar. 6, 2009

(87) PCT Pub. No.: WO2008/028667
PCT Pub. Date: Mar. 13, 2008

(65) Prior Publication Data
US 2010/0015215 A1    Jan. 21, 2010

(30) Foreign Application Priority Data
Sep. 7, 2006    (EP) .................................... 06018723

(51) Int. Cl.
*A61K 9/127*    (2006.01)
(52) U.S. Cl. ........................... 424/450; 424/489
(58) Field of Classification Search .................. None
See application file for complete search history.

(56) References Cited

FOREIGN PATENT DOCUMENTS

| | | |
|---|---|---|
| EP | 0 510 356 | 10/1992 |
| WO | WO 99/52549 | 10/1999 |
| WO | WO 03/009812 | 2/2003 |
| WO | WO 2004/009125 | 1/2004 |
| WO | WO 2004/028475 | 4/2004 |
| WO | WO 2006/027685 | 3/2006 |

OTHER PUBLICATIONS

Vajdy, M., et al. "Mucosal adjuvants and delivery systems for protein,-DNA- and RNA-based vaccines". Immunology and Cell Biology. vol. 82, No. 6. Dec. 2004. pp. 617-627.
Singh, M., et al. "Advances in vaccine adjuvants". Nature Biotechnology, vol. 17, No. 11. Nov. 1999. pp. 1075-1081.
Yang, Ya-Wun., et al. "The apoptotic and necrotic effects of tomatine adjuvant". Vaccine, Butterworth Scientific. vol. 22, No. 17-18. Jun. 2, 2004, pp. 2316-2327.
Milkereit, G., et al. "Synthesis and mesomorphic properties of glycosyl dialkyl- and diacyl-glycerols bearing saturaed, unsaturated and methyl branched fatty acid and fatty alcohol chains Part II. Mesomorphic properties". Chemistry and Physics of Lipids, Limerick, Ir. vol. 135, No. 1. May 2005. pp. 15-26.
Westwood, A., et al. "Activation of dendritic cells by microparticles containing *Bacillus anthracis* protective antigen". Vaccine, Butterworth Scientific. vol. 23, No. 29. May 31, 2005. pp. 3857-3863.
Rajananthanan, P., et al. "Evaluation of novel aggregate structures as adjuvants: composition, toxicity studies and humoral reposnses". Vaccine, Butterworth Scientific. vol. 17, No. 7-8. Feb. 26, 1999. pp. 715-730.

*Primary Examiner* — Frederick Krass
*Assistant Examiner* — Snigdha Maewall
(74) *Attorney, Agent, or Firm* — Whitman Curtis Christofferosn & Cook, PC

(57) ABSTRACT

The present invention relates to adjuvants of the glycolipid type and their uses in pharmaceutical compositions, like in vaccines. In particular, the present invention provides new uses of compounds useful as adjuvants for prophylactic and/or therapeutic vaccination in the treatment of infectious diseases, inflammatory diseases, autoimmune diseases, tumors and allergies. The compounds are particularly useful not only as systemic, but preferably as mucosal adjuvants.

9 Claims, 15 Drawing Sheets

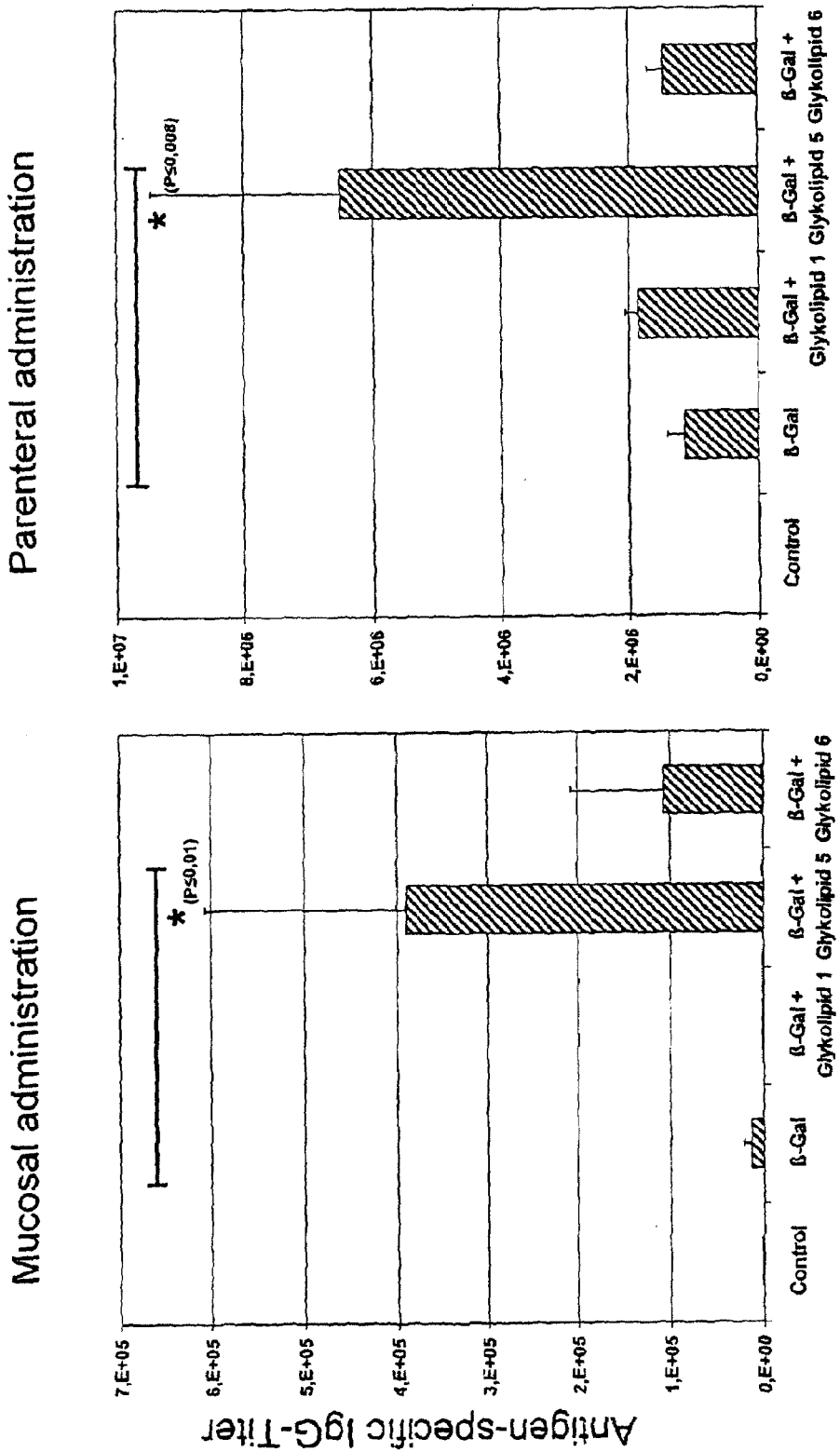
Fig. 3 (Glycolipids 1, 5 and 6: 10 μg/animal/immunisation)

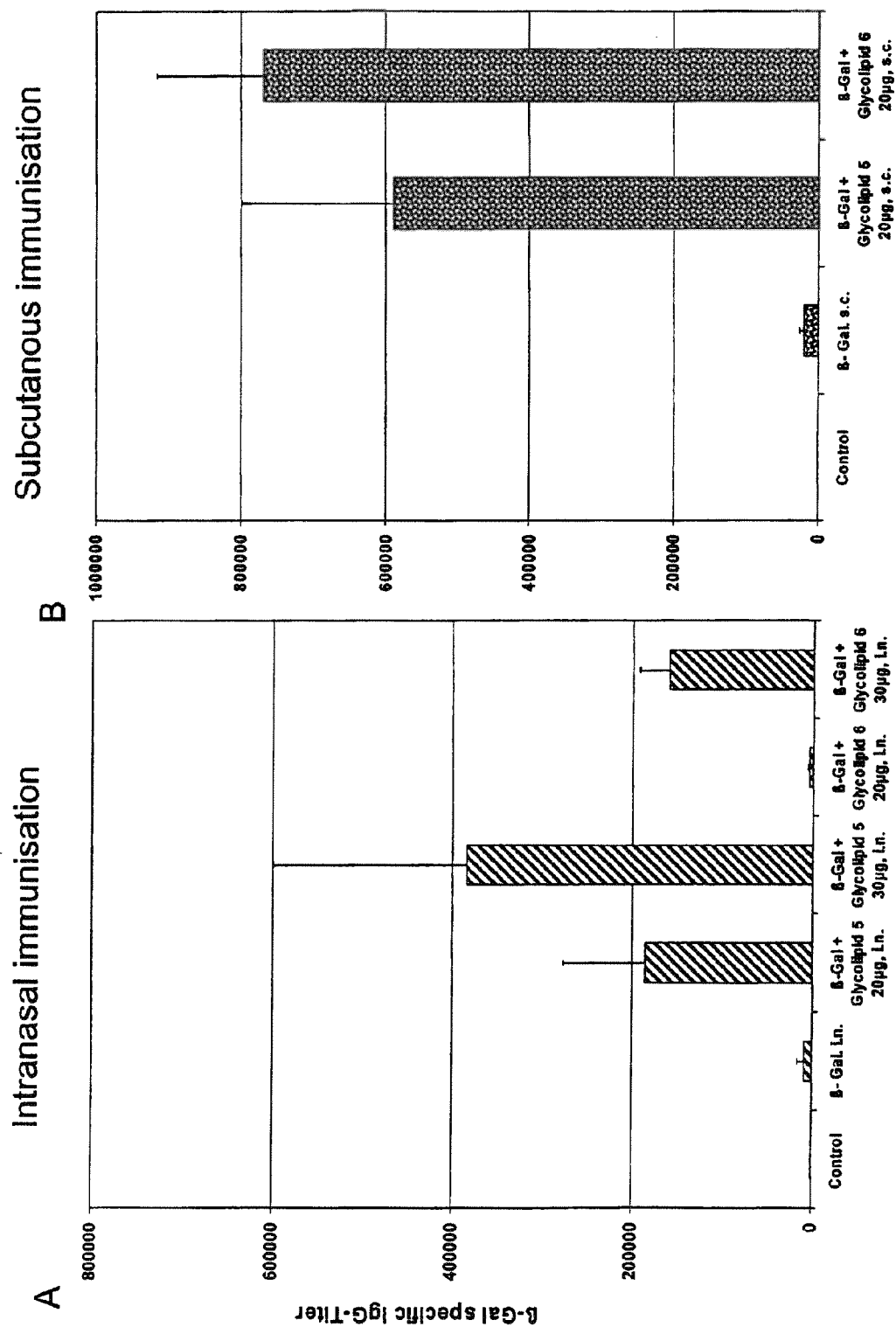
Fig. 4 (Glycolipids 5 and 6: 20 or 30 μg/animal/immunisation)

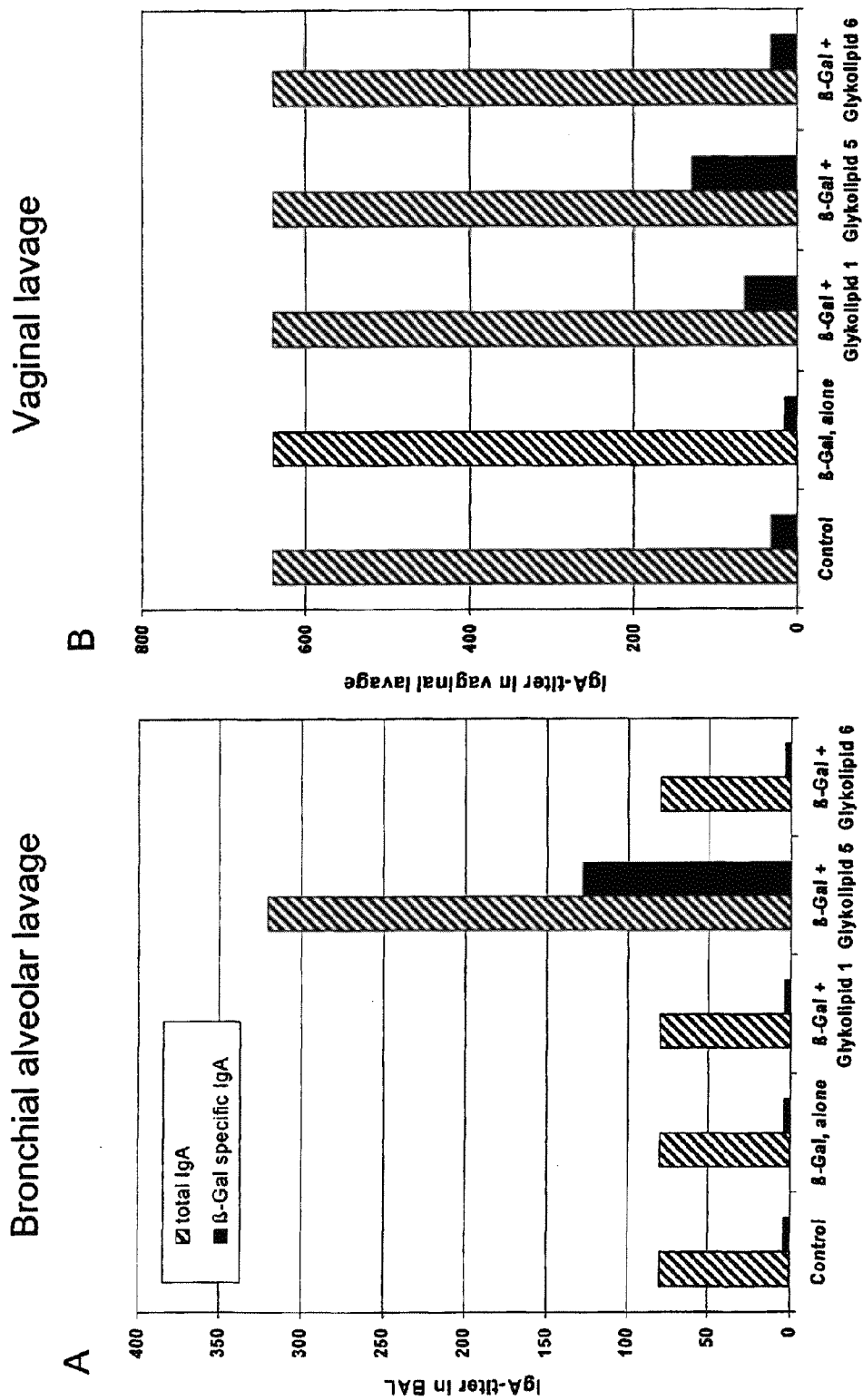
Fig. 5 (Glycolipids 1, 5 and 6: 10 µg/animal/immunisation)

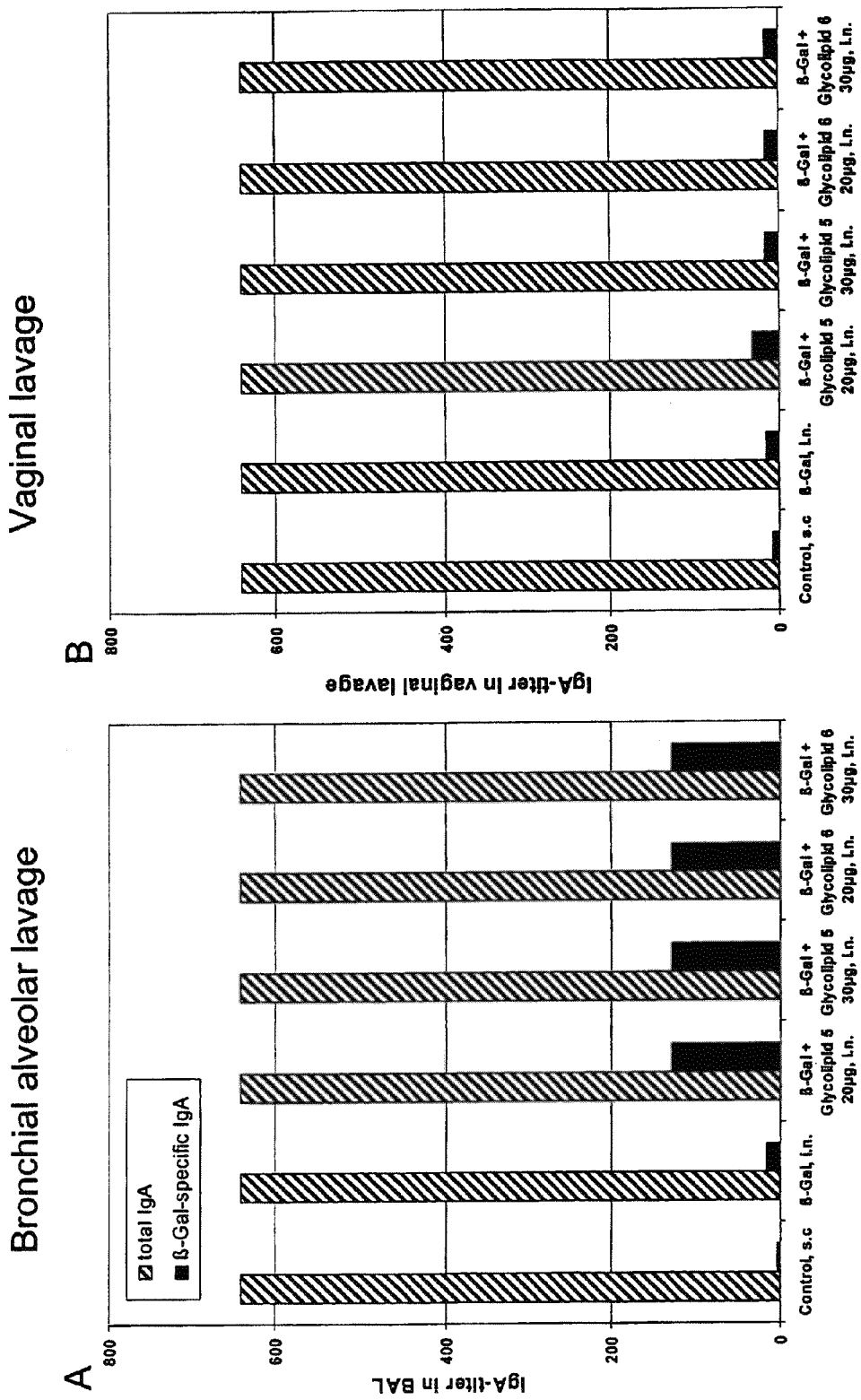
Fig. 6 (Glycolipids 5 and 6: 20 or 30 μg/animal/immunisation)

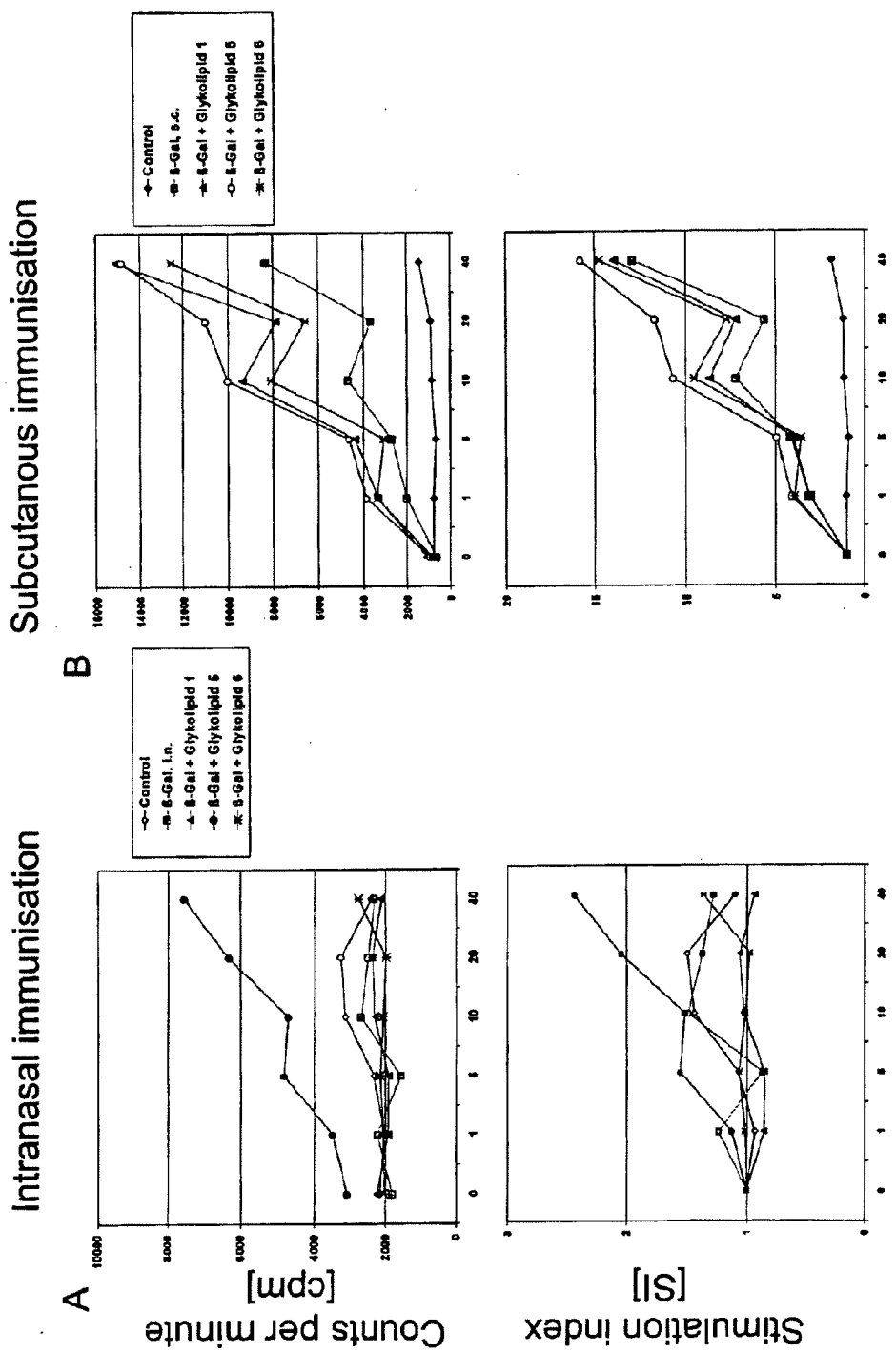
Fig. 7 (Glycolipids 1, 5 and 6: 10 μg/animal/immunisation)

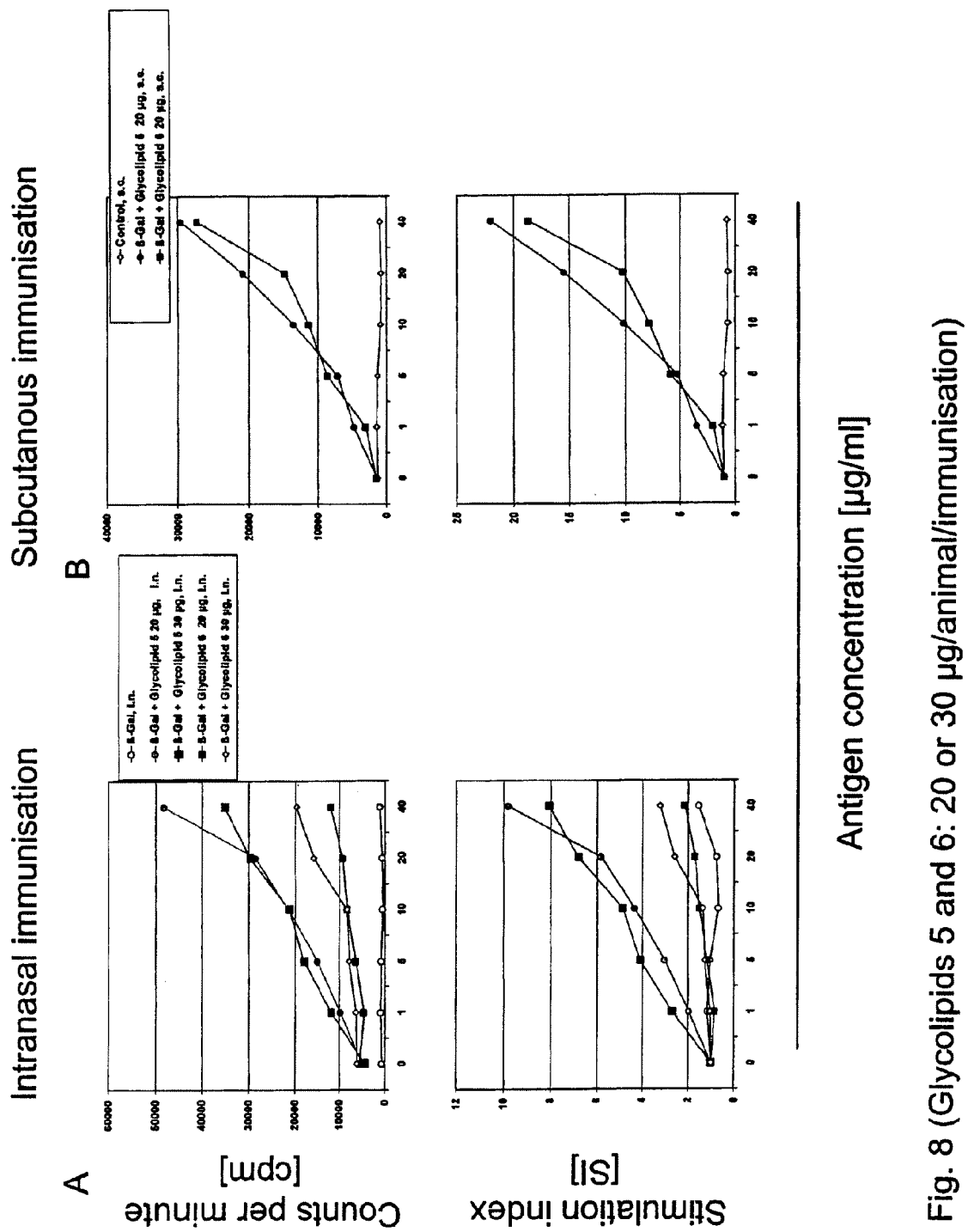
Fig. 8 (Glycolipids 5 and 6: 20 or 30 µg/animal/immunisation)

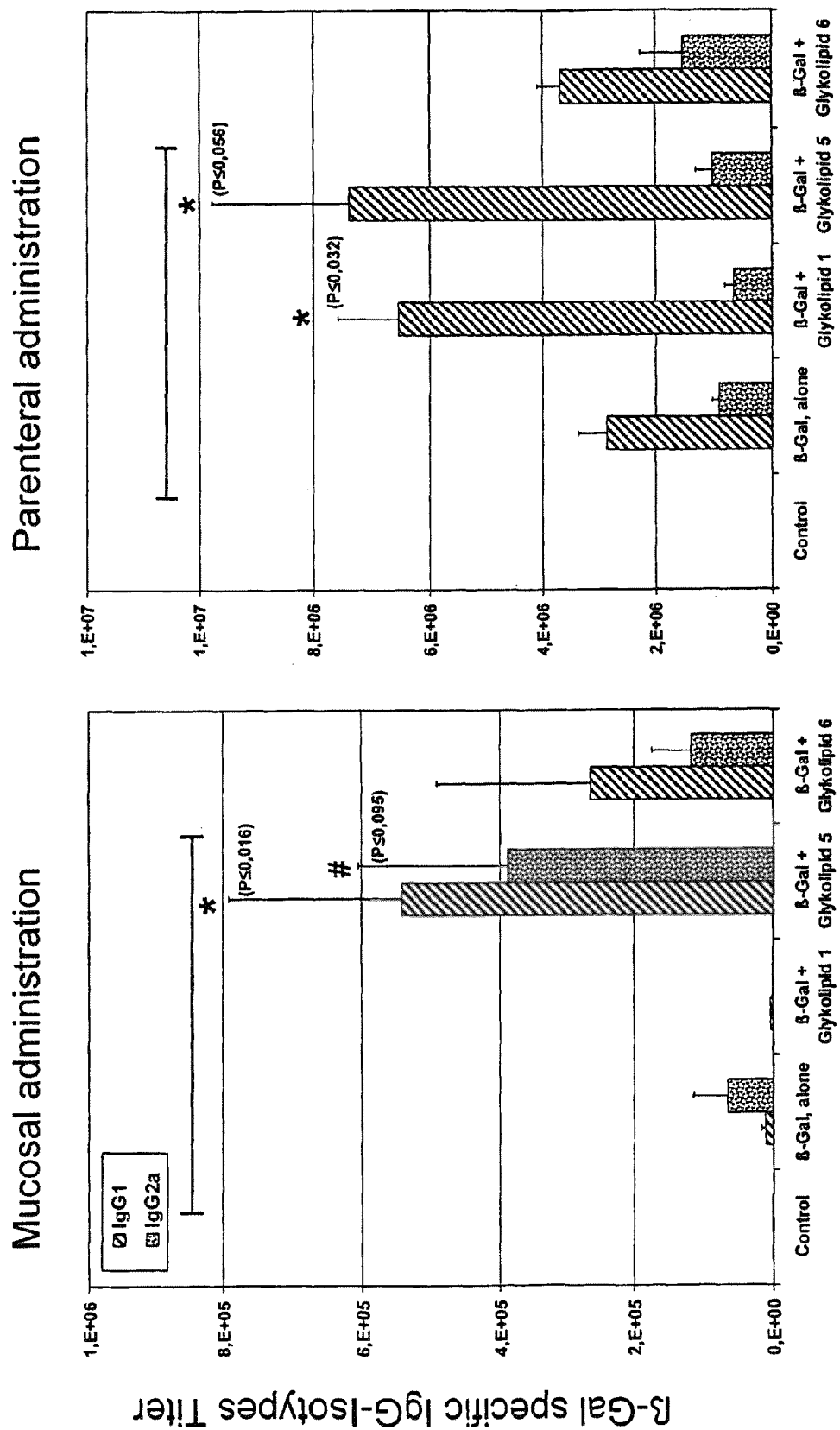
Fig. 9 (Glycolipids 1, 5 and 6: 10 μg/animal/immunisation)

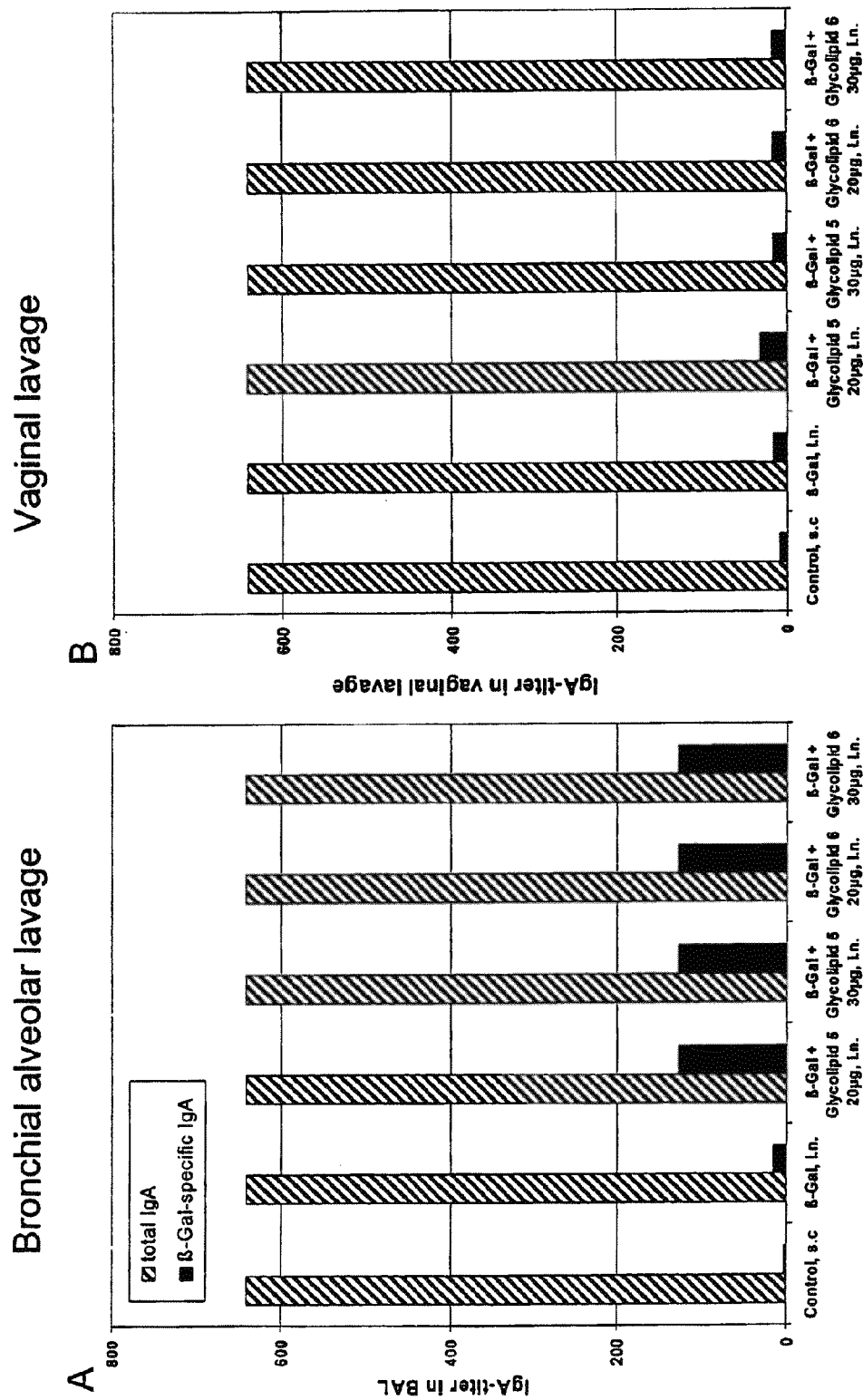
Fig. 10 (Glycolipids 5 and 6: 20 or 30 µg/animal/immunisation)

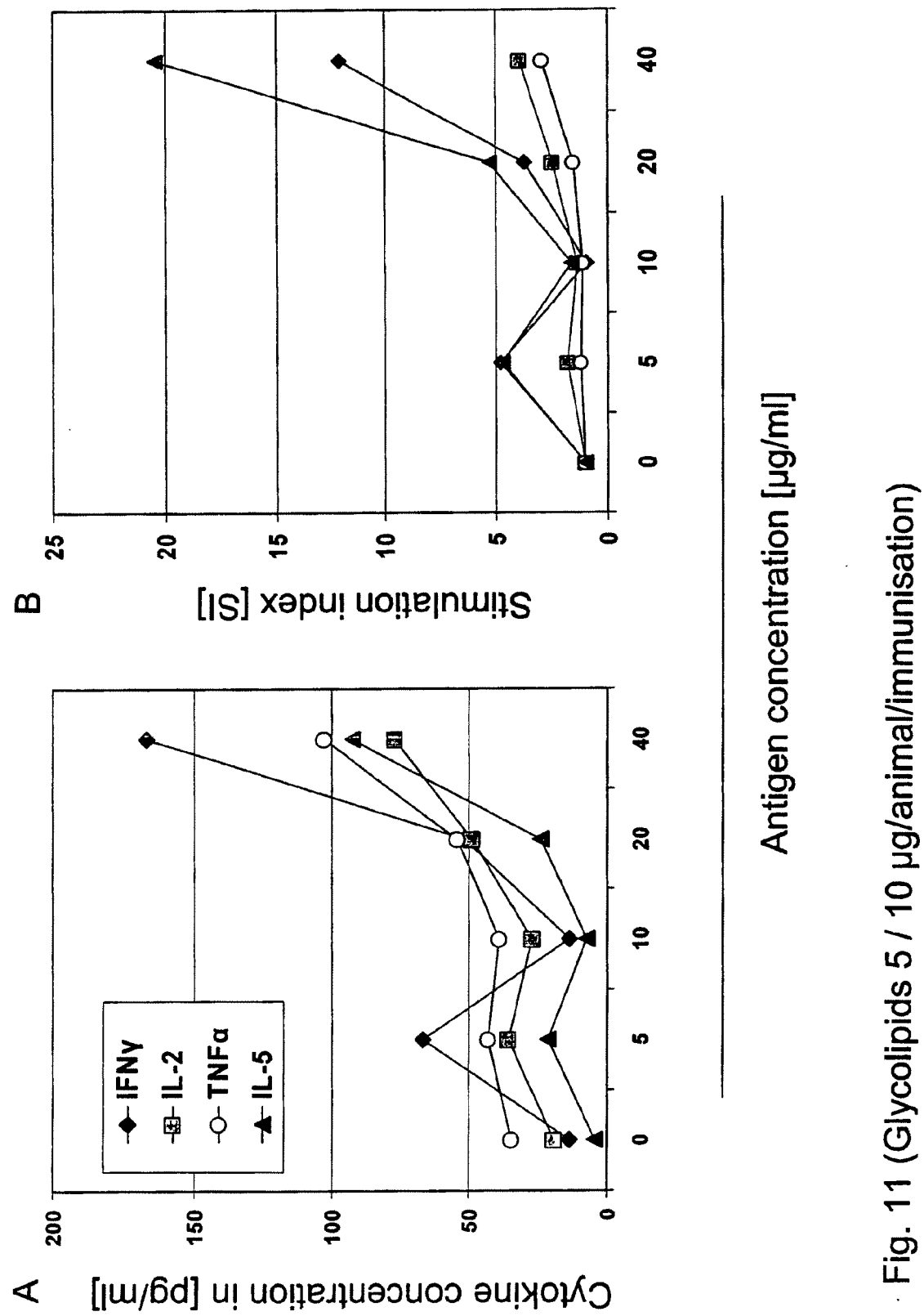
Fig. 11 (Glycolipids 5 / 10 µg/animal/immunisation)

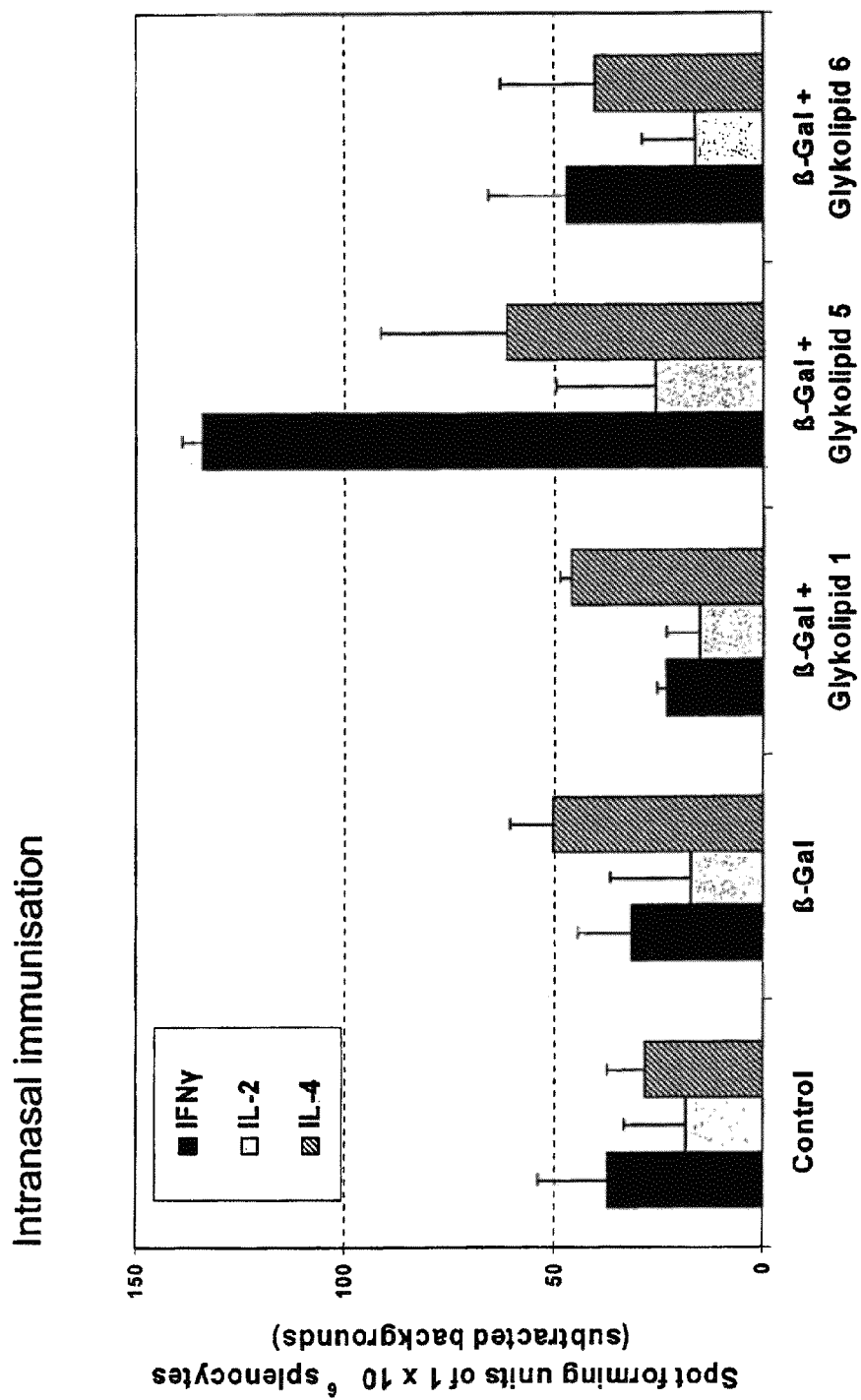
Fig. 12 (Glycolipids 1, 5 and 6: 10 μg/animal/immunisation)

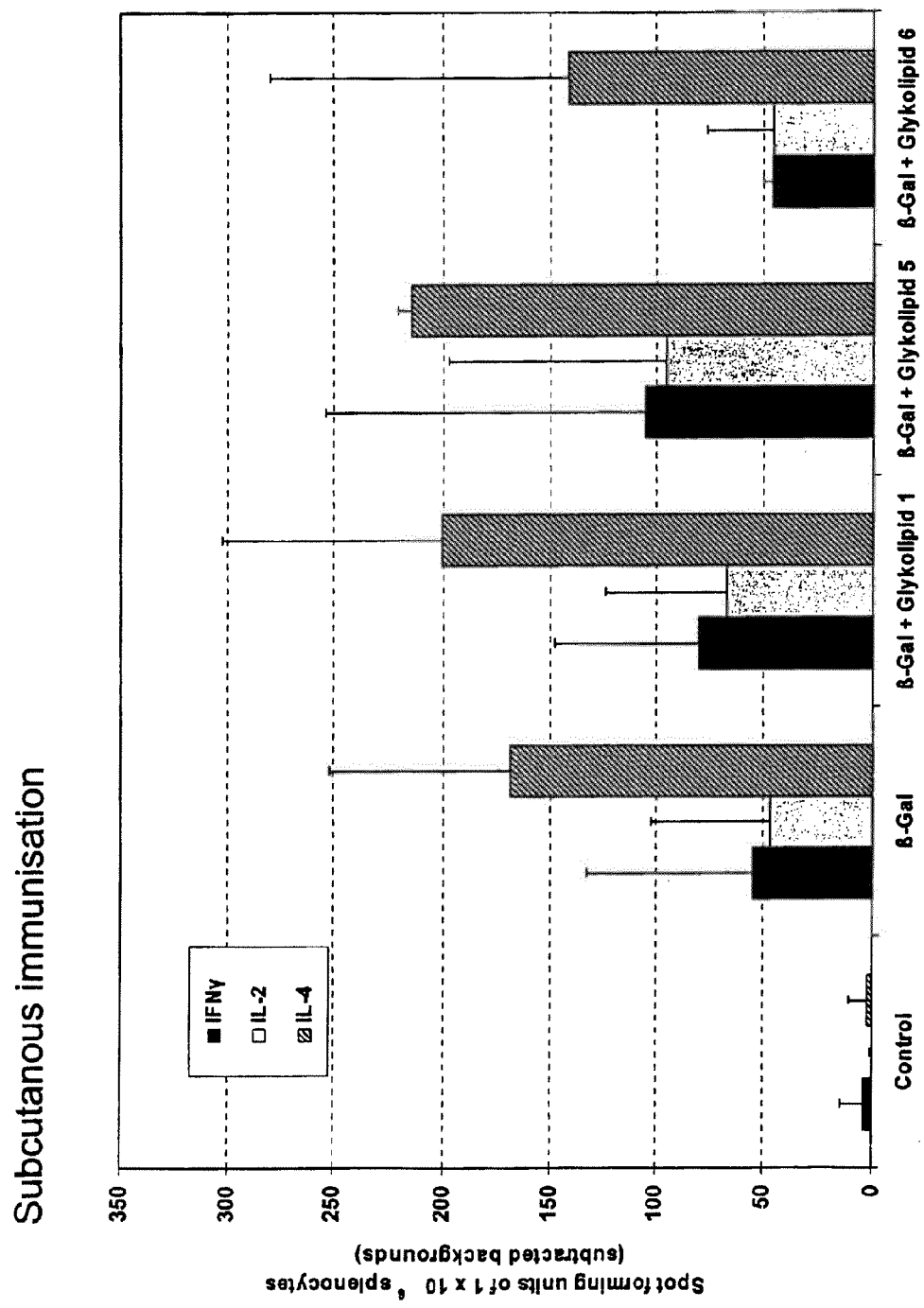
Fig. 13 (Glycolipids 1, 5 and 6: 10 μg animal/immunisation)

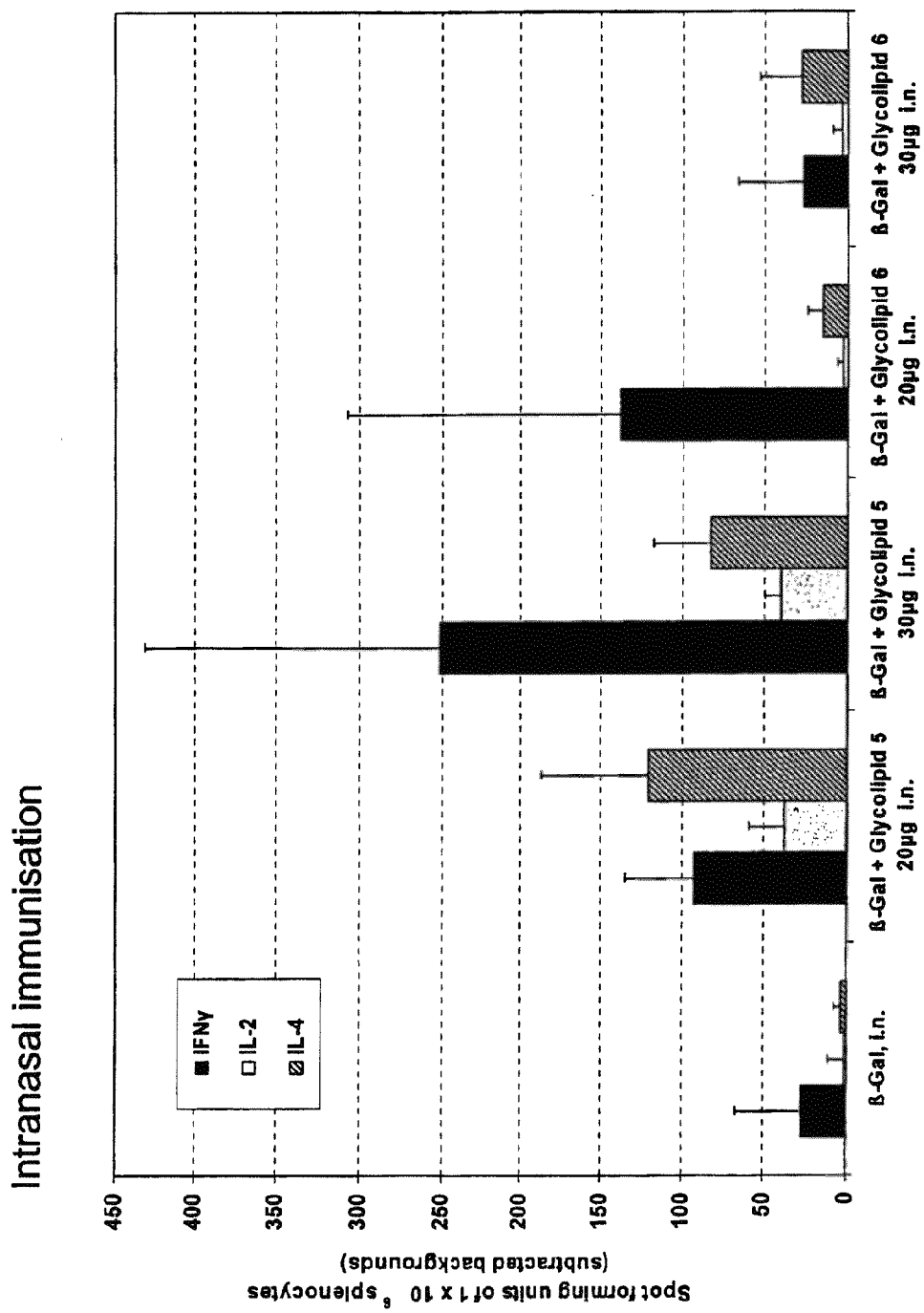
Fig. 14 (Glycolipids 5 and 6: 20 or 30 μg/animal/immunisation)

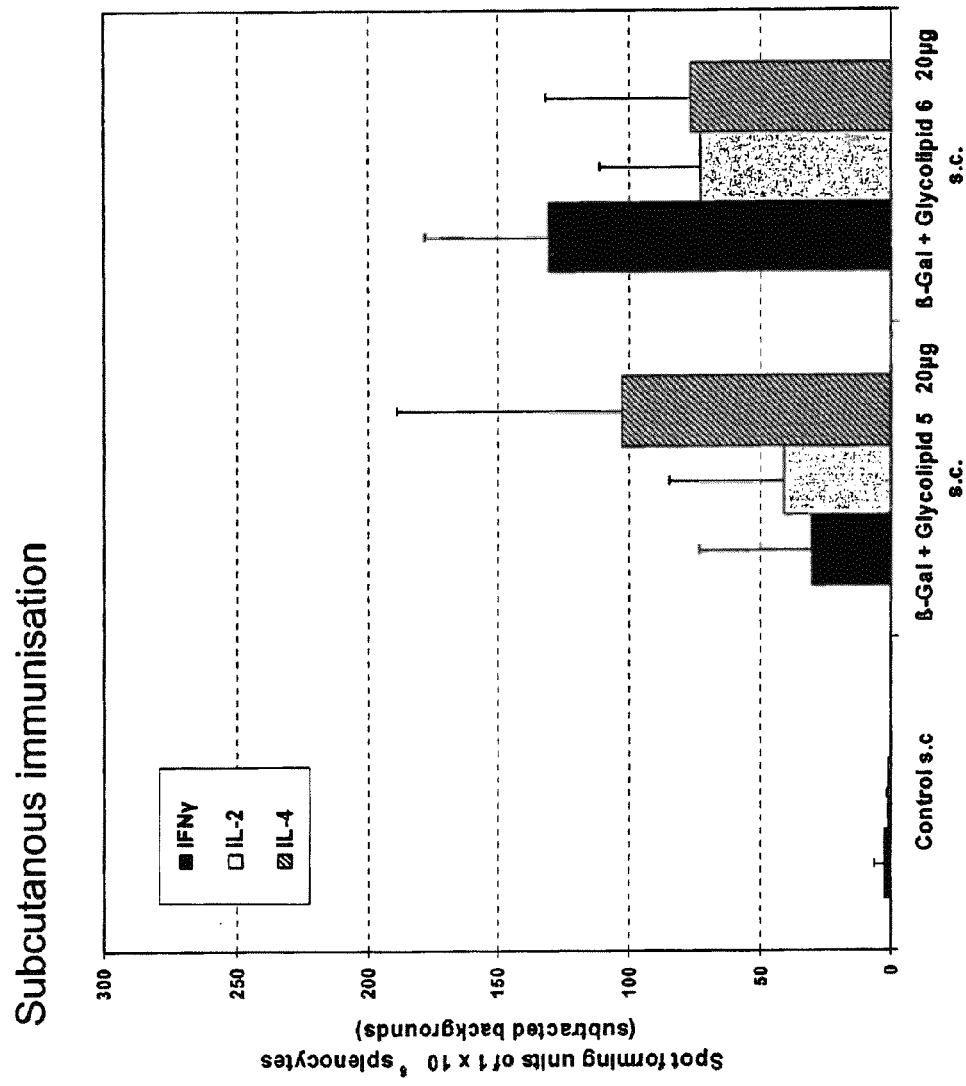
Fig. 15 (Glycolipids 5 and 6: 20 or 30 µg/animal/immunisation)

USE OF GLYCOLIPIDS AS ADJUVANTS

FIELD OF THE PRESENT INVENTION

The present invention relates to adjuvants of the glycolipid type and their uses in pharmaceutical compositions, like in vaccines. In particular, the present invention provides new uses of compounds useful as adjuvants for prophylactic and/or therapeutic vaccination in the treatment of infectious diseases, inflammatory diseases, autoimmune diseases, tumours, allergies as well as for the control of fertility in human or animal populations. The compounds are particularly useful as mucosal adjuvants. However, they are also effective as systemic adjuvants. In addition, the invention relates to its uses as active ingredients in pharmaceutical compositions.

BACKGROUND OF THE INVENTION

Infectious diseases are the major cause of morbidity and mortality, accounting for a third of the deaths which occur in the world each year. In addition, infectious agents are directly responsible for at least 15% of new cancers, and they also seem to be involved in the pathophysiology of several chronic diseases (e.g. inflammatory, vascular and degenerative diseases). Traditional infectious diseases are also highly expensive in terms of health-associated costs of infected patients and loss in productivity at work.

The main strategies used to prevent infectious diseases are therapy and prophylaxis. Vaccination has become the most cost-effective measure to prevent infections. However, there are still many diseases for which vaccines are not yet available or the available vaccines are not completely satisfactory due to low efficacy, high reactogenicity, poor stability and/or high costs. Thus, there is still an urgent need for both new and improved vaccines.

Despite the fact that vaccines have traditionally been used for the prophylaxis of infectious diseases, recent findings suggest that they are also a powerful tool for the immunotherapy of transmissible diseases (e.g. viral hepatitis, *Helicobacter pylori* infections, herpes virus infections, etc.). In addition, vaccines can be used for the immune-therapy or immune-prophylaxis of autoimmune diseases, inflammatory diseases, tumours, allergies and for the control of fertility in human and/or animal populations. In particular, the last application seems to require the elicitation of efficient mucosal responses at the level of the reproductive tract.

Immunotherapy is the synonym for a therapy using the own immune system to attack the disorder or disease. For example immunotherapy for cancer stimulate the own immune system to attack the tumour. Typically, immunotherapy involves the use of cytokines or antibodies for treating cancer. All kind of cancer may be treated, like solid tumours or metastases. Immunotherapy is also possible for infectious diseases. Usually immunomodulators or adjuvants are required to induce a sufficient response and to stimulate the immune system of the treated individual.

Typically, costimulatory molecules are important to elicit a sufficient immune response and to obtain a satisfactory prophylactic or therapeutic treatment of a disease or disorder. For example, relevant costimulatory molecules are CD80 and CD86 as well as CD54 or CD40L. Further soluble molecules, in particular cytokine and chemokines play an important role. Thus, a balanced orchestra of costimulatory molecules is necessary to achieve favourable immune responses in the prophylaxis or treatment of various diseases and disorders, e.g. in vaccines.

Most infectious diseases are either restricted to the mucosal membranes or the etiologic agents need to transit the mucosa during the early steps of the infection. Therefore, it is desirable to obtain not only a systemic, but also a local mucosal immune response as a result of vaccination, thereby blocking both infection (i.e. colonization) and disease development. This may result in a more efficient protection against infection, facilitating also the eradication of diseases for which humans are the only reservoirs (i.e. blocking transmission to susceptible hosts). Parenterally-administered vaccines mainly stimulate systemic responses, whereas vaccines administered by a mucosal route mimic the immune response elicited by natural infections and can lead to efficient mucosal and systemic responses. Due to the apparent compartmentalization of the systemic and mucosal immune system, parenterally administered vaccines are less effective in protecting against mucosal pathogens (McGhee, J. R., Mestecky, J., Dertzbaugh, M. T., Eldridge, J. H., Hirasawa, M. and Kiyono, H. (1992) The mucosal immune system: from fundamental concepts to vaccine development. Vaccine 10, 75-88). Thus, administration of immunogens through the mucosal route is required to achieve full protection. However, most of the available vaccines are administered through the parenteral route, thereby, eliciting a systemic immunity in the individual.

The administration of vaccines via the mucosal route offers several advantages over parenteral vaccination. These advantages include an ease of administration, the possibility of self-administration (e.g. by intranasal, rectal or oral application), the elimination of the chance of unwanted cross-infection due to the use of infected needles or non-sterile working, lower rates of side effects, higher acceptance by the public, better compliance of vaccination protocols (i.e. increment in the overall efficacy), simpler administration logistics and lower delivery costs, being particularly suitable for mass immunization programmes. However, the compartmentalisation at the level of the mucosal immune system has to be taken into consideration. In fact, immune responses which can be observed following intra-nasal vaccination may not necessarily occur after oral or intra-rectal immunisation. For example, oral vaccination may not stimulate efficient responses in the genitourinary and/or respiratory tracts.

Unfortunately, the delivery of antigens by the mucosal route is associated with a major problem, namely that antigens delivered by this route are generally poorly immunogenic. This is the result of different mechanisms, such as (i) accelerated antigen elimination by the non specific host clearance mechanisms (e.g. ciliar activity, peristaltism), (ii) antigen degradation by local enzymes, (iii) antigen alteration and/or structural modification as a result of extreme pH (e.g. acidic in the stomach, alkaline in the intestine), (iv) poor antigen penetration through the mucosa, (v) limited access of vaccine antigens to antigen presenting cells, and (vi) local peripheral tolerance.

To overcome these problems, different strategies have been used, such as antigen entrapment or association with physical or biological particles (e.g. microparticles, nanoparticles, bacterial ghosts), the use of virosomes or viral-like-particles, the use of liposomes or ISCOMS, the use of transgenic plants, antigen production by attenuated viral or bacterial carriers acting either as conventional vectors or as carriers for nucleic acid vaccines and/or their administration with mucosal adjuvants. However, despite the heavy body of experimental evidence generated in pre-clinical studies during the last years, almost no candidates have been transferred to the vaccine development pipeline.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response. In other words, an adjuvant can modulate the immune response or redirect the immune response to balance the immune response in the desired direction.

One major obstacle is to be able to induce systemic as well as mucosal responses to mucosal vaccines. Furthermore, other approaches, such as mucosally induced tolerance also seems to be a promising form of immunomodulation for treating certain autoimmune diseases and allergies. Improved biochemical techniques have allowed purifying and/or constructing of new and well characterised adjuvants. Recent advances in our understanding of the immune system, most particularly with respect to early pro-inflammatory signals, have led to the identification of new biological targets for vaccine adjuvants. In particular, one can now choose immuno-potentiating adjuvants for Protein- and DNA-based vaccines, able to selectively induce T helper (Th)-1 and/or Th2 responses, according to the vaccine target and the desired immune response. As our knowledge of the cell types and cytokines interacting in the immune responses increases, so does our understanding of the mode of action of adjuvants, as well as the way in which they produce adverse effects.

Substances referred to as "adjuvants" are those which are added and/or co-formulated in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag 1995). That is, adjuvants are compounds having immunopotentiating properties, in particular, when co-administered with antigens. The use of many adjuvants is based solely on experience, and the effect can neither be accurately explained nor predicted. The following groups of adjuvants are traditionally used in particular: aluminum hydroxide, emulsions of mineral oils, saponins, detergents, silicon compounds, thiourea, endotoxins of gram-negative bacteria, exotoxins of gram-positive bacteria, killed or attenuated living bacteria or parts thereof.

As noted above, administration of antigen in combination with suitable adjuvants generally permits use of a much smaller amount of antigen and increases the antibody titer. However, most of the adjuvants presently used in vaccination suffer in their properties regarding (bio)safety, biodegradability, stability, ease of mixing and use, broad range of antigens and administration routes as well as on economic and reliable production.

An overview over the presently known mucosal adjuvants and delivery systems, e.g. the above mentioned particles, ICOMS, liposomes and viral-like particles, for protein-DNA- and RNA-based vaccines is given in Vajdy et al., Immunol. Cell Biol., 2004, 82, 617-627. Therein the currently available approaches in immunopentiation of mucosal vaccines are discussed.

That is, various mucosal adjuvants have been described which should serve as an alternative for the adjuvants useful for systemic administration, e.g. see Vajdy et al., supra. These mucosal adjuvants include heat labile enterotoxin and detoxified mutants thereof. In particular, genetically detoxified mutants of heat labile enterotoxin of *E. coli* have been developed as useful mucosal adjuvants. Moreover, cholera toxin of vibrio cholera is known as an adjuvant useful for mucosal vaccination. Further, the application of unmethylated CpG dinucleotides has been described. It was shown that CpG can bias the immune response towards a Th1 response and can modulate pre-existing immune responses. Saponins are also described as immunomodulatory substances, predominantly via the induction of specific cytokines which then modulate and/or activate the immune response.

In addition, as adjuvants which may be useful in mucosal vaccination the following have been described:

The MALP-2 molecule and Bisaxcyloxypropylcysteine-conjugates thereof, e.g. a Bispalmitoyloxypropylcysteine-PEG molecule is known to represent potent stimulants for macrophages. The usefulness of MALP-2 as an adjuvant was shown previously, see e.g. WO2004/009125 and WO2003/084568. In particular, it was demonstrated that MALP-2 can act as an effective mucosal adjuvant enhancing the mucosal immune response, e.g. fostering an enhanced expression of antigen-specific IgA antibodies.

Furthermore, it was shown that MALP-2 can activate dendritic cells and B-cells, both play an important rule in the induction of a specific humoral immune response. In addition preliminary studies demonstrate that a combination for biologically active HIV-1 that protein and synthetic MALP-2 may be a promising vaccine with the MALP-2 component as an effective mucosal adjuvant.

Unfortunately, most of the compounds described above being useful as mucosal adjuvants are not utilisable due to their intrinsic toxicity, e.g. retrograde homing to neuronal tissues of bacterial toxoids and/or toxins at/in the derivatives after nasal vaccination. Other reasons for the inapplicability of most of the known adjuvants are their lack in (bio)safety, biodegradability, stability, broad range of application etc as noted above.

Thus, none of these previously described mucosal adjuvants have been approved yet, but, today, only two systemic adjuvants received approval to be administered to humans and, hence, are used for the preparation of human vaccines. These adjuvants are Alum and MF59. However, both are not effective as mucosal adjuvants.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found, as outlined above.

Glycopolymers are sugar-containing compounds, which may consist of repeating units of mono- or oligosaccharides (chemical glycopolymers) or which are sugar-containing macromolecules which in aqueous suspensions form polymeric aggregates (physical glycopolymers). Of course, the chemical glycopolymers may also be able to form physical glycopolymers. The glycoconjugates, glycolipids and glycoproteins, belong to the latter class of physical glycopolymers, as the most important group. The biological importance of this class has become evident only in the last 20 years. Glycolipids are essential constituents of cellular membranes with a large of number of functions. They may act as receptors, may provide specific contact, be important for cell aggregation and dissociation, and may transmit and receive signals, for example, to initiate cell division. Cerebrosides and monoacylglycosides belong to the simple glycolipids, and gangliosides belong to the more complex glycolipids, which usually have specialized functions as e.g. as cell surface receptors. Many glycolipids are known to modulate the immune response. In common nomenclature also bacterial lipopolysaccharides (LPS, endotoxins) belong to this class. LPS induce a variety of biological effects in mammals like activation of mononuclear cells to produce cytokines such as tumor necrosis factor and interleukins. Glycoproteins, i.e., proteins with a covalently linked carbohydrate moiety, are also ubiquitous in nature. They are found in cell membranes and inside cells, in the cytoplasm as well as in subcellular organelles and in extracellular fluids [Brandenburg K., et al., Carbohydrate Research 2003, 338 (23), 2477-2489].

Glyco glycero lipids are known to be an important class of glycolipids. These lipids can be found as important constituents in cell membranes. In principle, these lipids consist of a carbohydrate head-group as polar head while the unpolar tail is build up by glycerol esters or ethers of alkyl or acyl chains [Sing, N., et al., J. Immunol 1999, 163 (5), 2373-2377]. Lipids with small headgroups (1-3 carbohydrate units in the head) can be found as major components of the cell membrane, whereas the more complex lipids are involved in cell surface recognition processes [Brandenburg, supra].

In view of the known adjuvants described above, there is still a need to provide new compounds useful as adjuvants, particularly as mucosal adjuvants, and/or as vaccines. In particular, there is a need for mucosal adjuvants which can elicit a strong immune response which represent a balanced and/or adjusted immune response involving both humoral and cellular components, thus, allowing effective prophylaxis or treatment of various diseases and conditions, specifically of infectious diseases or cancer.

Thus, the object of the present invention is the provision of mucosal adjuvants which can elicit and/or enhance and/or modulate (pre-existing) immune response in an individual or subject. In particular, the invention was based on the object of developing a range of novel, highly active adjuvants, particularly mucosal adjuvants which are non-toxic for humans and which can be employed with a wide variety of active ingredients to be assisted in conventional or novel vaccines such as, in particular, prophylactic or therapeutic vaccines, including cancer and DNA vaccines.

Citation of any document herein is not intended as admission that such document is pertinent prior art, or considered material to the patentability of any claim of the present application.

DESCRIPTION OF THE INVENTION

This technical problem is solved by the provision of the embodiments as characterized in the claims.

The present invention is generally concerned with the provision of compounds and conjugates as depicted in formula (I) or formula (II) or salts or solvates thereof, useful as immunomodulatory compounds, in particular, as adjuvants, preferably as mucosal adjuvants. Furthermore, the present invention relates to new pharmaceuticals comprising at least one of the compounds or conjugates according to formula (I) or formula (II) as described herein with pharmaceutically acceptable carrier(s), optionally together with further active ingredients.

In addition, the present invention relates to new pharmaceuticals comprising at least one of the compounds or conjugates according to formula (I) or formula (II) or salts or solvates thereof as described herein as an adjuvant with pharmaceutically acceptable carrier(s) together with further active ingredients.

That is, the present invention relates to the provision of the use of specific compounds or conjugates useful as adjuvants in therapeutic or prophylactic vaccination. Said compounds and conjugates are useful as systemic and are particularly useful as mucosal adjuvants being applied via the mucosa of the individual.

The present inventors found that specific forms of glycolipids or conjugates thereof are particularly useful as adjuvants in vaccines for therapeutic or prophylactic vaccination. In particular, compounds as described herein demonstrate the applicability as parenteral adjuvants and, in particular, as mucosal adjuvants at low doses.

The term vaccine as used herein refers not only to vaccinations intended to induce prophylaxis but include vaccination for therapeutic purposes as well.

As used herein, the term "adjuvant" means substances which are added and/or co-formulated in an immunization to the active antigen, i.e. the substance which provokes the desired immune response, in order to enhance or elicit or modulate the humoral and/or cell-mediated (cellular) immune response against the active antigen.

Preferably, the adjuvant according to the present invention is also able to enhance or elicit the innate immune response. The mode of action include (i) enhancement of immunological half-life of the co-administered vaccine antigen, (ii) increased antigen uptake and presentation and/or (iii) modulatory effects. Herein adjuvants do not include delivery systems not having any immunostimulatory activity but delivery systems which have beside their property to act as delivery systems also display immunomodulating activity.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of an effective amount of a drug, among others.

As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes, polyoma-like particles, attenuated viruses, killed virus and virus-like particles.

As used herein, the term "pegylated" refers to the conjugation of a compound moiety with conjugate moiety(ies) containing at least one polyalkylene unit. In particular, the term pegylated refers to the conjugation of the compound moiety with a conjugate moiety having at least on polyethylene glycol unit.

As used herein, the term "mucosal" refers to mucosal surface from the body such as the nasal, oral, gastro-enteric, rectal, urinary, conjunctial, glandular, e.g. mammary gland, epithelial mucous.

As used herein, the term "conjugate" refers to compounds comprising a conjugate moiety and a compound moiety. The term "conjugate moiety" e.g. refers to substituent B of the general formula (II). The conjugate moiety aims to increase the applicability of the residual compound. In contrast, the term "compound according to formula (I)" or "compound moiety" refers to a compound of the general formula (I).

As used herein, the term "antigenic structure" or "antigen" refers to a structure capable of causing a cellular or humoral immune response. The antigenic structure, also known as epitope is the part of the antigen, which is presented by the MHC or MHC like molecules. Further, the epitope or antigenic structure represents the part of an antigen recognized by antibodies directed against said antigen.

As used herein, the term "modulate an immune response" refers to any change of the present state of the immune response. The immune response may be modulated insofar that the response is elicited or a preexisting immune response is enhanced or decreased. In addition, the immune response may be modulated by shifting the immune response from a more humoral to a more cellular immune response or vice versa. Further, the immune response may be modulated by switching or redirecting the response from a Th1 to Th2 or Th3 response or vice versa. In addition, the modulation of the immune response may encompass the activation or enhancement of the innate immune response.

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

With the term "which may be substituted" is meant a substitution with a $C_1$-$C_6$ alkyl group or a $C_1$-$C_6$ alkoxy group.

As used herein, the term "carrier" refers to a diluent, adjuvant, excipient, or vehicle.

Thus, according to the first embodiment, the present invention relates to the use of glycolipides of the general formula (I):

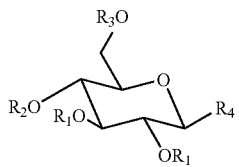

wherein $R_1$ is independently selected from the group of hydrogen, $C_1$ to $C_6$ alkyl- or $C_1$ to $C_6$ acyl-group which may be substituted;

$R_2$ is α-D-glycopyranosyl, α-D-galactopyranosyl, 4'-O-(α-D-glycopyranosyl)-α-D-glycopyranosyl, 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl which may be substituted and $R_3$ is hydrogen or $R_3$ is α-D-glycopyranosyl, α-D-galactopyranosyl, 4'-O-(α-D-glycopyranosyl)-α-D-glycopyranosyl, 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl which may be substituted and $R_2$ is hydrogen;

$R_4$ is

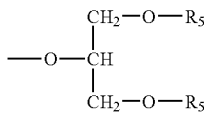

wherein $R_5$ is independently any one of a $C_5$ to $C_{30}$ alkyl- or alkenyl group which may be substituted; or salts or solvates thereof as a mucosal adjuvant. In another embodiment, the present invention relates to the compound of formula I as defined above as a systemic adjuvant.

In particular, the compound is useful as an adjuvant for therapeutic and/or prophylactic vaccination.

Further, the present invention relates to conjugates according to formula (II) having a compound moiety as shown in formula (I) and a conjugate moiety B. Said conjugates are particularly useful as a systemic or mucosal adjuvant. Preferably, said conjugates are used for therapeutic and/or prophylactic vaccination.

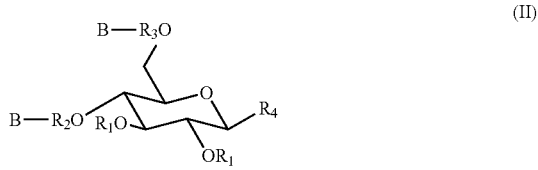

Preferably, in formula (I) and formula (II) $R_2$ is α-D-glycopyranosyl, α-D-galactopyranosyl, 4'-O-(α-D-glycopyranosyl)-α-D-glycopyranosyl 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl which may be substituted and $R_3$ is hydrogen.

$R_1$ in formula (I) or formula (II) is preferably hydrogen or an acetyl group.

$R_4$ in formula (I) or formula (II) is preferably

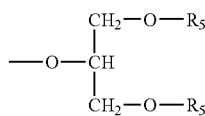

wherein $R_5$ is a $C_{10}$ to $C_{26}$, more preferably a $C_{12}$ to $C_{20}$, like a $C_{12}$, $C_{14}$, $C_{16}$, $C_{17}$, $C_{18}$ or $C_{20}$ alkyl- or alkenyl group. Particular preferred is $R_5$ an alkenyl group, like a cis-9-octadecenyl-group or an alkyl group, like $C_{14}$ alkyl, a tetradecyl group. In a preferred embodiment, the alkyl or alkenyl group is a methyl branched group. Methyl branched means that at least one of the carbon atoms of the alkyl or alkenyl group, preferably all carbon atoms, are substituted with a methyl group. $R_5$ may be different or identical.

Most preferred are the glycolipids:
1,3-di-O-(cis-9-octadecenyl)-2-O-[4'-O-(α-D-glycopyranosyl)-β-D-glycopyranosy]sn glycerol (compound 1 of FIG. 1);
1,3-di-O-(tetradecyl)-2-O-[4'-O-(α-D-glycopyranosyl)-β-D-glycopyranosy]sn glycerol (compound 5 of FIG. 1)I; and
methyl branched 1,3-di-O-(tetradecyl)-2-O-[4'-O-(α-D-galactopyranosyl)-β-D-glycopyranosy]sn glycerol (compound 6 of FIG. 1).

In particular, compound 1 of FIG. 1 demonstrates high potentials as a mucosal adjuvant.

The conjugate moiety B of the conjugate of formula (II) according to the present invention is a covalently bonded, physiologically tolerated conjugate moiety, which is suitable for converting the glycolipid into a more water-soluble form. For example, the conjugate moiety can be a polymer, a dextran, a sugar, a polyvinylpyrrolidone, an alginate, a pectin or collagen. The conjugate moiety is characterized in that it provides good water and is not immunogenic.

The conjugate moiety B of the glycolipid conjugate claimed herein, is in a preferred embodiment, a conjugate moiety containing at least one polyalkylene glycol unit of the formula:

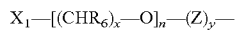

where
X$_1$ is hydrogen or a hydrocarbon which may contain heteroatom(s);
Z is a divalent linkage group, such as C=O or CHR$_6$ or PO$_3$
R$_6$ is independently any one of hydrogen, OH, OR$_7$ or CO—R$_8$;
R$_7$ is independently any one of hydrogen or C$_1$-C$_6$ alkyl;
R$_8$ is independently any one of hydrogen, OH, OR$_7$ or NR$_9$R$_{10}$;
R$_9$ and R$_{10}$ are independently any one of hydrogen or hydrocarbon which may contain heteroatom(s) and which may form a ring;
n is an integer of 1 to 100;
x is independently an integer of 1 to 10;
y is an integer of 0 to 10.
Preferably, n is an integer of 2 to 50, like 2 to 10, in particular 3 to 5.
y is preferred an integer of 1 to 5, in particular, 1 to 3, in another preferred embodiment, y is 0.
X$_1$ is preferentially OR$_{11}$, N(R$_{11}$)$_2$, SR$_{11}$ or COOR$_{11}$, wherein each R$_{11}$ is individually hydrogen, benzyl or C$_1$-C$_6$ alkyl, preferably a C$_1$-C$_6$ alkoxy group, like a methoxy, ethoxy or propoxy group.
R$_6$ is preferably a hydrogen atom.
Thus, the polyalkylene glycol unit mentioned above may preferably contain subunits of ethylene glycol, propylene glycol or butylene glycol or combinations thereof. The chain length of each of the polyalkylene glycol units may be in the range of 1 to 100 subunits, preferably, 2 to 50 subunits, like 2 to 10 subunits, particularly in the range of 3 to 5 subunits.
Particularly preferred is B a methoxypolyalkyleneglycolcarbonyl-residue wherein the alkylene moiety is an ethylene or propylene moiety.
Hence, in one embodiment preferably the conjugates are in a pegylated form to increase the solubility in hydrophilic solvents and hydrophilic environment. Furthermore, the conjugate moiety allows protecting the compound moiety, i.e. the active mucosal adjuvant moiety, against enzymatic degradation, structural modification due to change of the pH, mechanical removal, etc. Thus, primarily the stability of the compound is increased. Another beneficial effect of conjugation is to increase the retention time in the individual, e.g. to delay the renal excretion, while being well-tolerated, e.g. being non immunogenic, by said organism.
Specifically, the conjugate moiety comprises at least two chains having polyalkylene glycol units. That is, the conjugate may be a branched compound wherein each arm contains a polyalkylene glycol unit. Particularly preferred are conjugate moieties wherein the polyalkylene glycol unit is a polyethylene, polypropylene or polybutylene glycol unit.
In a particularly preferred embodiment, the compound moiety according to formula (II) is covalently linked with the conjugate moiety being a branched moiety wherein at least two arms containing polyethylene glycol units having 3 to 5 ethylene glycol subunits and a methoxy group at the free end of the polyethylene group. In particular, the branched moiety comprises 4 or 6 arms each having 3 ethylene glycol subunits and a methoxy group at the free end of the polyethylene group.

In particular, the glycolipid conjugate is characterized in that the conjugate B is 4armPEG ((S)-10-Amino-6,9,13,16-tetraoxo-N,N',8,14-tetrakis(3,6,9,12-tetraoxatridec-1-yl)-5,8,14,17-tetraazahenicosane-1,21-diamide), 6armPEG or 8armPEG, see also http://ww.celares.com. Other suitable conjugate moiety comprising at least one polyethylene unit are obtainable e.g. from celares GmbH, Berlin, see http://www.celares.com.
Said conjugate may be covalently bonded with any one of the oxygen atoms present at positions 2, 3, 4 and/or 6 of the carbohydrate residue. Preferably, the conjugate moiety is bonded at position 2 or 3. In another preferred embodiment, only one conjugate moiety B is present per glycolipide, although two or more are conceivable.
The compounds or conjugates of formula (I) or Formula (II) may be in the form of pharmaceutically acceptable non-toxic salts thereof. Salts of formula (I) or of formula (II) include acid added salts, such as salts with inorganic acids (e.g. hydrochloric acid, sulphuric acid, nitric acid and phosphoric acid) or with organic acids (e.g. acetic acid, propionic acid, maleic acid, olec acid, palmitic acid, citric acid, succinic acid, tartaric acid, fumaric acid, glutamic acid, panthothenic acid, laurylsulfonic acid, methanesulfonic acid and phthalic acid).
The compounds or conjugates of formula (I) or formula (II) may be in the form of solvates thereof (e.g., hydrates).
The compounds and conjugates as described above can additionally used as an immunomodulator in a pharmaceutical composition for preventing or treating infectious diseases, cancers, tumours, autoimmune diseases or allergies, or chronic or acute inflammatory processes or to control fertility in human or animal populations. The synthesis of conjugates may be conducted by methods known to the person in the art. For example, a hydroxyl group may be converted into a halogen residue, e.g. Cl, Br, I and this residue can react with modified conjugates having a free amino-group. For example, synthesis of pegylated conjugates are described in Veronese F. M., Biomaterials 22 (2001), 405-417 and Kodera Y., et al., Prog. Polym. Sci. (1998), 23, 1233-1271 which are incorporated herein by reference.
In a preferred embodiment, the compound(s) or conjugate(s) according to formula (I) or formula (II) or salts or solvates thereof are useful as mucosal adjuvant(s), in particular, for intranasal, intra NALT, oral, intra-rectal, conjunctival, intra-vaginal, intrathecal, intrabronchial, intrapulmonary, or intra-urethral administration, administration into the milk ducts of the breast or by inhalation.
Particularly preferred is the intranasal administration or the administration by inhalation using suitable aerosol formulations. Aerosol formulations useful for administration of vaccines are known in the art.
The compounds or conjugates according to formula (I) or formula (II) or salts or solvates thereof are also suitable as systemic adjuvant(s). Thus, the adjuvants described herein are also applicable as parenteral adjuvant(s), in particular, in subcutaneous, intravenous, intradermal, topical or intramuscular administration.
The adjuvant of the invention can be linked by all methods known to the skilled person to the antigen or active molecule intended for the vaccination, be incorporated together with the latter in physical (e.g. microparticles, nanoparticles, liposomes, ISCOMS, polymers) or biological particles (bacteria, bacterial parts) or virosomes or be mixed with the antigen. For binding to carriers it is also possible to provide transport molecules or transport proteins as carriers.
The compound(s) or conjugate(s) according to the formula (I) or formula (II) or salts or solvates thereof is/are preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastro-intestinal tract. Alternatively, the mucosal adjuvant of the invention can be present in a kit for co-administration with a vaccine by one of the aforementioned routes and be adapted therefore where appropriate. That is the vaccine may be administered simultaneously, sequentially or separately with the active vaccination component.

In another embodiment, the present invention relates to methods of treating individuals afflicted with a disease or condition that can be treated by modulating the immune response comprising administering to said individual an effective amount of a pharmaceutical comprising the compounds or conjugates according to formula (I) or formula (II), salts and solvates thereof as defined herein as an adjuvant, particularly as a mucosal adjuvants together with an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The compounds or conjugates or salts or solvates thereof as defined herein are particular useful as mucosal adjuvants for activating or enhancing in vitro and/or in vivo the antigen presenting function of antigen presenting cells for a therapeutic or prophylactic intervention. That means, the adjuvants can stimulate macrophages, can stimulate or enhance the humoral immune response, e.g. enhancing or stimulating the production of antibodies. In addition, the adjuvants can also enhance or stimulate the cellular immune response, e.g. increasing the proliferation of T-cells. Further the compounds or conjugates of formula (I) or formula (II) or salts or solvates thereof can not only activate or stimulate components of the adaptive immune system but also of the innate immune system, like activating NK-cells or NKT-cells. In addition, it is possible to use the adjuvant(s) for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Thus, in case of the use of the compounds or conjugates or salts or solvates thereof as defined herein as an adjuvant, the pharmaceutical composition according to the present invention is preferably a vaccine, comprising said compounds or conjugates or salts or solvates thereof as pharmaceutically acceptable adjuvant(s) together with the active vaccination component (e.g. the antigen) and, optionally, a pharmaceutically acceptable carrier, diluent, preservative, adjuvant other than the adjuvant according to the present invention, immunomodulator or excipient.

The active vaccination component may be any component suitable to elicit, enhance or modulate an immune response in an individual. The active vaccination component is suitable particularly for intranasal, intra-NALT, oral, intra-rectal, conjunctival, intra-vaginal, aerosolized or intra-urethral administration, or administration into the milk ducts of the breast.

For example, the active vaccination component, the active ingredient of the pharmaceutical composition, comprises at least one or more different antigens in the form of peptides, proteins, polysaccharides, glycolipids or DNA encoding them or bacterial ghost, virosomes, or attenuated vaccines.

Preferentially, the antigen(s) are tumour antigen(s) or antigen(s) derived from infectious agents. The infectious agents include those agents which normally enters individual's organism by crossing the mucous membrane.

The pharmaceutical composition comprising adjuvant(s) according to the present invention, an active vaccination component, optionally additional carrier, diluent, preservative, adjuvant other than the adjuvant according to the present invention, immunomodulator or excipient may additionally contains components, like compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

However, the compounds and conjugates according to formula (I) or formula (II), salts and solvates thereof as defined herein for the use as adjuvants may also be a component of a pharmaceutical composition provided in a formulation suitable for parenteral administration, in particular, in subcutaneous, intravenous, intradermal or intramuscular administration.

Further, the compounds according to the present invention are useful in tumour therapy including the in vitro generation or in vitro priming of autologous cells for adoptive cell transfer in tumour therapy and transplantation. Moreover, the adjuvants are useful for the induction of cross-tolerance against microbial components, like endotoxins, to protect against septic shock or other severe forms of diseases induced by microbial components.

In addition, the compounds themselves as defined herein may display a pharmaceutical activity, e.g. are to be useful in the prophylaxis and treatment of various diseases and conditions, like cancer, infectious diseases, septic shock, chronic and inflammatory processes, autoimmune diseases, allergies, etc.

Hence, the compounds and conjugates according to formula (I) or formula (II) or salts or solvates thereof are also useful for the preparation of a pharmaceutical to prevent or treat infectious diseases, septic shock, cancer, tumours, autoimmune diseases, allergies, or chronic or acute inflammatory processes.

The conjugates according to the present invention and salts or solvates thereof, particularly, the pegylated conjugates, can be used as active ingredients in pharmaceuticals useful for the prevention or treatment of infectious diseases, septic shock, tumours, autoimmune diseases, allergies, or chronic or acute inflammatory processes. In particular, the conjugates or salts or solvates thereof are contained in pharmaceuticals useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, helicobacter pylori, herpes virus, etc.; bacterial infections, such as tuberculosis, leprosy and listeriosis, and parasitic infections such as malaria.

Thus, in a further aspect, the present invention relates to pharmaceutical compositions comprising compounds or conjugates according to formula (I) or formula (II) or salts or solvates thereof, in particular, conjugates containing at least one conjugate moiety comprising a polyalkylene glycol unit, as defined herein or salts or solvates thereof and, optionally, a pharmaceutically acceptable carrier. Such pharmaceutical compositions comprise a therapeutically effective amount of the conjugates and, optionally, a pharmaceutically acceptable carrier. The pharmaceutical composition may be administered with a physiologically acceptable carrier to a patient, as described herein. Acceptable means that the carrier be acceptable in the sense of being compatible with the other ingredients of the composition and not be deleterious to the recipient thereof. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin ($18^{th}$ ed., Mack Publishing Co., Easton, Pa. (1990)). Such compositions will contain a therapeutically effective amount of the aforementioned compounds according to formula (I) or formula (II), salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in the immunological responses to infection or a suppression of the responses to inflammatory processes.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the conjugates according to formula (I) or formula (II), salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In still another embodiment, the present invention relates to methods of treating individuals suffering from infectious diseases, septic shock, tumours, autoimmune diseases, allergies, or chronic or acute inflammatory processes comprising the step of administering to said individual an effective amount of a pharmaceutical comprising a compound or conjugate according to formula (I) or formula (II) or salts or solvates thereof as an adjuvant or active ingredient together with an active ingredient, and, optionally, a pharmaceutically acceptable carrier. In particular, the method is useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, helicobacter pylori, herpes virus, etc.; bacterial infections, such as tuberculosis, leprosy and listeriosis, and parasitic infections such as malaria.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle, preferably bacterial ghosts.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical compositions according to the present invention can be done in a variety of ways as discussed above, including, but not limited to, orally, subcutaneously, intravenously, intra-arterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 µg; however, doses below or above this exemplary range are envisioned, especially considering the aforementioned factors.

In still another aspect, the present invention relates to the use of the compound(s). or salts or solvates thereof as defined herein in a pharmaceutical preparation to control fertility in human or animal populations.

Finally, the present invention relates to kits comprising the compounds and/or conjugates as described in the present invention or salts or solvates thereof. In particular, the kit is useful for the preparation of pharmaceutical compositions in particular a vaccine. Optionally, the kit contains instructions for preparing the pharmaceutical composition, like the vaccine.

In a preferred embodiment thereof, the kit contains the glycolipid compound or conjugate according to the present invention or salts or solvates thereof as an adjuvant and an antigen comprising an antigenic structure and, optionally, a pharmaceutically acceptable carrier, diluent, preservative, adjuvants other than the conjugates according to the present invention, immunomodulators or excipient and instructions for preparing a vaccine.

In another preferred embodiment, the kit contains compounds and/or conjugates according to the present invention or salts or solvates thereof as an adjuvant and an antigen comprising an antigenic structure and, optionally, a pharmaceutically acceptable carrier, diluent, preservative, adjuvants other than the compounds or conjugates of formula (I) or formula (II), immunomodulators or excipients and, optionally instructions for preparing a vaccine.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.tiqr.orq/, are known to the person skilled in the art and can also be obtained using, e.g., http://www-.google.de. An overview of patent information in biotechnology and a survey of relevant sources of patent information useful for retrospective searching and for current awareness is given in Berks, TIBTECH 12 (1994), 352-364.

BRIEF DESCRIPTION OF THE FIGURES

FIG. 3.
Co-administration of β-Gal with 10 µg glycolipids 1, 5 and 6 induced β-Gal-specific systemic IgG responses in Balb/c mice. Balb/c mice were immunized by the i.n. or s.c. route with β-Gal alone or together with glycolipids 1, 5 and 6 three times at 2-wk intervals. 10 days after the final immunization, the immunized mice were sacrificed. The levels of β-Gal-specific systemic IgG were determined in Sera of mice immunized by the i.n. (A) and s.c. (B) route. The serum of mice immunized with β-Gal co-administered with glycolipids 1, 5 and 6 by the intranasal route showed a significant enhancement of β-Galactosidase-specific IgG (>200000) in comparison to animals which were immunized with β-Gal alone (<$^1$/$_{10000}$). The parenteral administration of with β-Gal co-administered with glycolipids 1, 5 and 6 doubled the β-Galactosidase-specific IgG titer (>500000) in comparison to animals which were immunized with β-Gal alone. Bars represent mean Ab titer or amount±SE in each group. Each group consists of five mice. Data are representative of three separate experiments.

FIG. 4.
Co-administration of β-Gal with 20 or 30 µg glycolipids 5 and 6, respectively induced β-Gal-specific systemic IgG responses in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. The levels of β-Gal-specific systemic IgG were determined in Sera of mice immunized by the i.n. (A) and s.c. (B) route. The serum of mice immunized with β-Gal co-administered with glycolipids 5 and 6 by the intranasal route showed a dose-dependent significant enhancement of β-Galactosidase-specific IgG (>600000) in comparison to animals which are immunized with β-Gal alone (<$^1$/$_{10000}$). The parenteral administration of with β-Gal co-administered with 20 µg glycolipids 5 and 6 enhanced the β-Galactosidase-specific IgG titer (>800000) in comparison to animals which were immunized with β-Gal alone. Bars represent mean Ab titer or amount±SE in each group. Each group consists of five mice. Data are representative of two separate experiments.

FIG. 5.
Co-administration of β-Gal with 10 µg glycolipids 1, 5 and 6 induced β-Gal-specific mucosal S-IgA responses in Balb/c mice. Balb/c mice were immunized by the i.n. or s.c. route with β-Gal alone or together with glycolipids 1, 5 and 6 three times at 2-wk intervals. 10 days after the final immunization, the immunized mice were sacrificed. β-Gal-specific S-IgA titers were determined in vaginal lavage (VL) and Bronchial alveolar lavage (BAL) of mice immunized with β-Gal co-administered with glycolipids 1, 5 and 6 by the intranasal route. Co-administration of glycolipid 5 showed a significant enhancement of β-Galactosidase-specific sigA titer (>1/130) in probes of the Bronchial alveolar lavages (A) in comparison to animals which were immunized with β-Gal alone or with the other glycolipids 1 and 6. Furthermore, these animals showed an enhanced β-Galactosidase-specific sIgA in vaginal lavages (B). Bars represent mean Ab titer or amount±SE in each group. Each group consists of five mice. Data are representative of three separate experiments.

FIG. 6.

Figure 1:
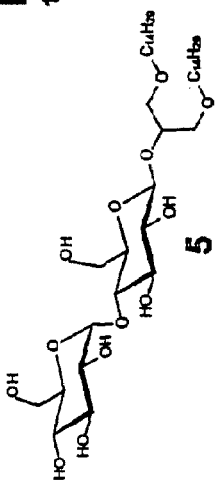
FIG. 1.
Chemical structure of the new glycolipid compounds 1 [Mal-1,3-oleyl], 5 [Mal-1,3-C14] and 6 [Mel-1,3-C14].
Figure 1:
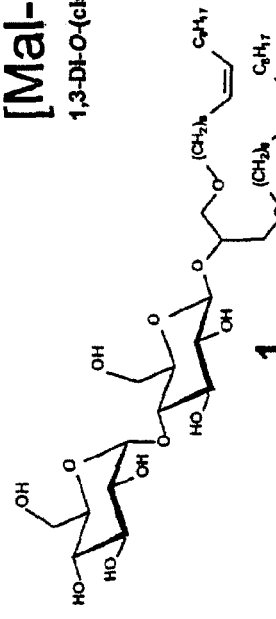
Figure 1:
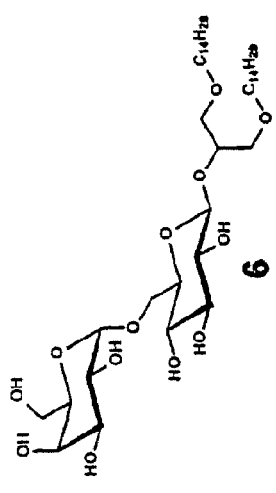

Co-administration of β-Gal with 20 up to 30 μg glycolipids 5 and 6 induced β-Gal-specific mucosal S-IgA responses in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. β-Gal-specific S-IgA titers were determined in vaginal lavage (VL) and Bronchial alveolar lavage (BAL) of mice immunized with β-Gal co-administered with glycolipids 5 and 6 by the intranasal route. Co-administration of glycolipid 5 showed a significant enhancement of β-Galactosidase-specific sIgA titer (>1/170 in probe of the Bronchial alveolar lavages (A) in comparison to animals which were immunized with β-Gal alone. Higher concentrations of glycolipid 6 induced comparable sIgA titers in BAL (A). The expression of β-Gal-specific S-IgA titers was comparable with titer of the control groups. Bars represent mean Ab titer or amount±SE in each group. Each group consists of five mice. Data are representative of three separate experiments.

FIG. 7.

Co-administration of β-Gal with 10 μg glycolipids 1, 5 and 6 induced a strong cellular immune responses against the β-Gal antigen in Balb/c mice. Balb/c mice were immunized by the i.n. or s.c. route with β-Gal alone or together with glycolipids 1, 5 and 6 three times at 2-wk intervals. 10 days after the final immunization, the immunized mice were sacrificed. Splenocytes of mice immunized by the i.n. (A) and s.c. (B) route were collected and cultured with different concentrations of the β-Gal-Protein for 4 days. The spleen cells of mice immunized with β-Gal co-administered with glycolipids 5 by the intranasal route showed a significant enhanced [3H]thymidine incorporation in response to enhanced antigen concentration (SI>2,5), whereas the co-administration of glycolipids 1 and 6 and β-Gal alone showed no effect. The parenteral administration of with β-Gal co-administered with glycolipids 1, 5 and 6 showed enhanced [3H]thymidine incorporation in response to enhanced antigen concentration (SI>12) in comparison to animals which were immunized with β-Gal alone (B). Curves represent [³H]thymidine incorporation (counts per minute, cpm) and Stimulation index (SI) in each group. Each group consists of five mice. Data are representative of three separate experiments.

FIG. 8

Co-administration of β-Gal with 20 up to 30 μg glycolipids 5 and 6 induced a strong cellular immune responses against the β-Gal antigen in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. Splenocytes of mice immunized by the i.n. (A) and s.c. (B) route were collected and cultured with different concentrations of the β-Gal-Protein for 4 days. The spleen cells of mice immunized with β-Gal co-administered with glycolipids 5 by the intranasal route showed a dose-dependent enhanced [3H] thymidine incorporation in response to enhanced antigen concentration (SI>8), whereas the co-administration of glycolipids 6 showed only a weak stimulation index (SI>3) with highest concentration (30 μg per animal). The parenteral administration of with β-Gal co-administered with glycolipids 5 and 6 showed enhanced [3H]thymidine incorporation in response to enhanced antigen concentration (SI>15) in comparison to animals which were immunized with β-Gal alone (B). Curves represent [3H]thymidine incorpoaration (counts per minute, cpm) and Stimulation index (SI) in each group. Each group consists of five mice. Data are representative of three separate experiments.

FIG. 9

Co-administration of β-Gal with 10 μg glycolipids 1, 5 and 6 induced β-Gal-specific systemic IgG responses in Balb/c mice. Balb/c mice were immunized by the i.n. or s.c. route with β-Gal alone or together with glycolipids 1, 5 and 6 three times at 2-wk intervals. 10 days after the final immunization, the immunized mice were sacrificed. The levels of β-Gal-specific titers of IgG isotypes were determined in Sera of mice immunized by the i.n. (A) and s.c. (B) route. The serum of mice immunized with β-Gal co-administered with glycolipid 5 by the intranasal route showed a significant enhancement ($P \leq 0.01$) of β-Galactosidase-specific IgG secretion (29× fold by i.n. and 7-fold by s.c. administration) in comparison to animals which are immunized with β-Gal alone. Animals immunized with glycolipid 6 by the i.n. route showed an 8-fold increase, whereas the glycolipid 1 showed no effect in comparison to animals which are immunized with β-Gal alone. The analysis of the antigen specific IgG-isotype titer in sera showed that animals immunized with β-Gal co-administered with glycolipid 5 by intranasal route had a significant enhancement ($P \leq 0.016$ and $P \leq 0.095$) of β-Gal-specific IgG1 (50-fold) and IgG2a (6-fold) secretion in comparison to animals which are immunized with β-Gal alone. Animals immunized with glycolipid 6 by the i.n. route showed an 24-fold increase in IgG1 secretion and a 1.8-fold increase in IgG2a secretion in comparison to animals which are immunized with β-Gal alone, whereas glycolipid 1 had no effect. The parenteral administration of β-Gal co-administered with glycolipid 1 or glycolipid 5 showed a significant enhancement ($P \leq 0.032$ and $P \leq 0.056$) of β-Gal specific IgG1 secretion (2.5-fold and 2.2-fold increase, respectively), whereas glycolipid 6 showed no effect. Furthermore, there was no enhanced secretion of IgG2a isotype observed. Bars represent mean Ab titer or amount±SE in each group. Each group consists of five mice. Data are representative of three separate experiments.

FIG. 10

Co-administration of β-Gal with 20 or 30 μg glycolipids 5 and 6, respectively, induced β-Gal-specific systemic IgG responses in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. The levels of β-Gal-specific titers of IgG isotypes were determined in Sera of mice immunized by the i.n. (A) and s.c. (B) route. The serum of mice immunized with β-Gal co-administered with glycolipids 5 and 6 by the intranasal route showed a dose-dependent enhancement of β-Galactosidase-specific IgG2a isotype (7-fold increase) in comparison to animals which were immunized with β-Gal alone. Furthermore, animals immunized with the glycolipid 6 showed a comparable expression of IgG1 and IgG2a isotypes. The parenteral administration of with β-Gal co-administered with 20 μg glycolipids 5 and 6 enhanced the β-Galactosidase-specific IgG1 isotype titer (>250000) in comparison to animals which were immunized with β-Gal alone. Bars represent mean Ab titer or amount±SE in each group. Each group consists of five mice. Data are representative of two separate experiments.

FIG. 11

Co-administration of β-Gal with 10 μg glycolipid 5 represented both Th1 and Th2 cytokine profiles activities in Balb/c mice. 10 days after the final immunization, the immunized Balb/c mice were sacrificed. A total of $5 \times 10^6$ cells/ml were stimulated with different concentrations of the β-Gal antigen for 4 days, and the levels of IFNγ and IL-4 in the supernatant were examined by the BD Cytometric bead array. Cytokine production of the spleen cells were analyzed using BD CBA kit according to the manufacturer's instructions. The spleen cells of mice immunized with β-Gal co-administered with glycolipid 5 by the intranasal route showed enhanced expression of proinflammatory (TNFα), Th1 (IFNγ and IL-2) and Th2 (IL-5) cytokines in response to enhanced concentrations of the β-Gal antigen, shown by the enhanced stimulation index (B). Curves represent cytokine concentration (pg/ml) and Stimulation index (SI) in response to enhanced antigen concentration in each group. Each group consists of five mice. Data are representative of two separate experiments.

FIG. 12/13

Co-administration of β-Gal with 10 μg glycolipids 1, 5 and 6 induced a strong cellular immune responses and enhanced levels of IFNγ, IL-2 and IL-4 in response to enhanced concentration of the β-Gal antigen in Balb/c mice. Balb/c mice were immunized by the i.n. or s.c. route with β-Gal alone or together with glycolipids 1, 5 and 6 three times at 2-wk intervals. 10 days after the final immunization, the immunized mice were sacrificed. Splenocytes of mice immunized by the i.n. (FIG. 12) and s.c. (FIG. 13) route were collected and cultured with different concentrations of the antigen. A total of $5 \times 10^6$ cells/ml spleen cells were cultured with 2 μg/ml of the MHC cI.I restricted β-Gal peptide (IFNγ) for 24 h and the β-Gal-Protein (IL-2 and 4) for 48 h. IFNγ producing CD8+ T cells were analyzed using BD Elispot kit according to the manufacturer's instructions. The spleen cells of mice immunized with β-Gal co-administered with glycolipid 5 by the intranasal route showed enhanced expression of spot forming units (SFU) secreting IFNγ in response to the antigen, whereas the co-administration of glycolipids 1 and 6 showed only a weak secretion of IFNγ. The parenteral administration of with β-Gal co-administered with glycolipids 1, 5 and 6 showed only weak enhanced secretion of IFNγ, IL-2 and IL-4 in response to the β-Gal antigen in comparison to animals which were immunized with β-Gal alone. Bars represent Spot forming units of $10^6$ splenocytes with subtracted background mean SFU±SE in each group. Each group consists of five mice. Data are representative of three separate experiments.

FIG. 14/15

Co-administration of β-Gal with 20 up to 30 μg glycolipids 5 and 6 induced strong cellular immune responses and enhanced levels of IFNγ, IL-2 and IL-4 in response to enhanced concentration of the β-Gal antigen in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. Splenocytes of mice immunized by the i.n. (FIG. 14) and s.c. (FIG. 15) route were collected and cultured with different concentrations of. A total of 5×106 cells/ml spleen cells were cultured with 2 μg/ml of the MHC class I restricted β-Gal peptide (IFNγ) for 24 h and the β-Gal-Protein (IL-2 and 4) for 48 h. IFNγ producing CD8+ T cells were analyzed using BD Elispot kit according to the manufacturer's instructions. The spleen cells of mice immunized with β-Gal co-administered with glycolipid 5 by the intranasal route showed enhanced expression of spot forming units (SFU) secreting IFNγ in a dose dependent matter in response to the antigen, whereas the co-administration of glycolipid 6 showed a reduced cytokine secretion in response to the β-Gal antigen. The parenteral administration of with β-Gal co-administered with glycolipids 5 and 6 showed only a minor effect in the secretion of IFNγ, IL-2 and IL-4 in response to the β-Gal antigen in comparison to control animals. Bars represent Spot forming units of $10^6$ splenocytes with subtracted background mean SFU±SEM in each group. Each group consists of five mice. Data are representative of three separate experiments.

EXAMPLES

1. Synthesis of Glycolipids

The glycolipids were synthesized as described in Milkereit G., Brandenburg K., Gerber S., Koch M. H., Morr M., Andra L., Seydel U., Vill V., Synthesis and mesomorphic properties of glycosyl dialkyl- and diacyl-glycerols bearing saturated, unsaturated and methyl branched fatty acid and fatty alcohol chains (Part II. Mesomorphic properties, Chem Phys Lipids, May 2005, 135(1):15-26) and Milkereit G., Gerber S., Brandenburg K., Morr M., Vill V., Synthesis and mesomorphic properties of glycosyl dialkyl- and diacyl-glycerols bearing saturated, unsaturated and methyl branched fatty acid and fatty alcohol chains (Part I. Synthesis, Chem Phys Lipids, May 2005, 135(1):1-14) which is incorporated herein by reference. In brief:

Materials and Methods

Peracetylated Disaccharides where prepared according to the literature (Vill, V., Bocker, T., Thiem, J., Fischer, F., Liq. Cryst., 6, 1989, 349-356). n-Tetradecanol (purest grade) and maltose monohydrate were purchased from Fluka Chemie. α-Melibiose monohydrate was purchased from Acros Organics.

Thin-layer chromatography was performed on silica gel (Merck GF254), and detection was effected by spraying with a solution of ethanol/sulfuric acid (9:1), followed by heating. Column chromatography was performed using silica gel (Merck, 0.063-0.200 mm, 230-400 mesh). NMR spectra were recorded on a Bruker AMX 400 or a Bruker DRX 5001 spectrometer (mc=centred multiplet, d=doublet, t=triplet, dd=double doublet, dt=double triplet).

Procedures for the preparation of the following compounds can be found in:

1,3-Di-O-tetradecyl-propantriol:

Bear, E., Stanacev, N. Z., J. Biol. Chem., 240, 1965, 44-48.

1,3-Di-O-(cis-9-octadecenyl)-propantriol:

Altenburger, J.-M., Lebeau, L., Mioskowski, C., Schirlin, D., Helv. Chim. Acta, 75, 1992, 2538-2544.

Paltauf, F., Johnston, J. M., Biochim. Biophys. Acta, 239, 1971, 47-56.

4-O-(2,3,4,6-Tetra-O-acetyl-α-D-glucopyranosyl)-2,3,6-tri-O-acetyl-α-D-glucopyranosyl-trichloracetimidat:

Schmidt, R. R., Kinzy, W., Adv. Carbohydr. Chem. Biochem., 50, 1994, 21-123.

Deacetylation (General Procedure 1)

The compound was dissolved in anhydrous methanol and sodium methoxide was added (pH 8-9). The solution was stirred at ambient temperature until TLC revealed the reaction to be complete. It was neutralised then using Amberlyst IR 120 ion-exchange resign (protonated form), filtrated and evaporated in vacuo.

1,3-Di-O-(cis-9-octadecenyl)-propan-2-ol (Compound 1)

To a solution of 50 mL (42.5 g; 186.2 mmol) cis-9-octadecen-1-ol in 100 mL of dry toluene 4.3 g (186 mmol) sodium was added in small portions. The solution was stirred at 80° C. for 20 hours until all of the sodium had been dissolved. After cooling to room temperature 7.6 mL (10.3 g; 80 mmol) 1,3-Dichlorpropan-2-ol in 50 mL of dry toluene were added dropwise over a period of 60 minutes. The solution was stirred for an additional 2 hours at 40° C. Afterwards the reaction was quenched with first 2-propanol, then methanol and finally water. The organic layer was washed with 0.1 m hydrochloric acid (50 mL), twice with Brine (80 mL) and finally with water (50 mL). The organic layer was dried over anhydrous magnesium sulfate, and the solvent was removed under reduced pressure. The residue was chromatographed on silica gel (light petroleum b.p. 50-70° C.—ethyl acetate 6:1) to give a yellow syrup.

Yield: 9.9 g (21%).

1H-NMR (400 MHz, CDCl3+TMS): δ=5.28-5.43 (m, 4H, H-olefin.), 3.94 (mc, 1H, H-2), 3.39-3.52 (m, 8H, H-1a, H-3a, H-3b, α-CH2), 2.08-2.92 (m, 8H, CH2-allyl.), 1.52-1.62 (m, 4H, β-CH2), 1.21-1.39 (m, 44H, Alkyl-CH2), 0.88 (t, 6H, Alkyl-CH3). 13C-NMR (100 MHz, CDCl3+TMS): δ=130.10 (C-olefin.), 72.15 (C-1, C-3), 71.18 (Alkyl-α-CH2), 70.13 (C-2), 32.57, 30.51, 30.26, 30.04, 29.89, 29.79, 29.71 (Alkyl-CH2), 23.36 (C-allyl.), 14.54 (Alkyl-CH3).

1,3-Di-O-tetradecyl-propan-2-ol (Compound 2)

To a solution of 10.7 g (50 mmol) tetradecan-1-ol in 130 mL of dry toluene 1.8 g (50 mmol) sodium was added in small portions. The solution was stirred under reflux for 2 days until all of the sodium had been dissolved. 2.3 g (1.95 mL; 50 mmol) epichlorhydrine were added dropwise. The solution was stirred for an additional 4 hours under reflux. The reaction was quenched with first 2-propanol, then methanol and finally water, and the solvent removed in vacuo. The residue was dissolved in 400 mL ether, washed with 0.1 m hydrochloric acid (100 mL) and twice with water (100 mL). The organic layer was dried over anhydrous magnesium sulfate, and the solvent was removed under reduced pressure. The residue was chromatographed on silica gel (light petroleum b.p. 50-70° C.—ethyl acetate 9:1) to give a white powder.

Yield: 6 g (50%).

1H-NMR (400 MHz, CDCl3+TMS): δ=3.84-3.90 (m, 1H, H-2), 3.34-3.44 (m, 8H, H-1a, H-1b, H-3a, H-3b, Alkyl-α-CH2), 1.50 (mc, 4H, Alkyl-α-CH2), 1.16-1.23 (m, 44H, Alkyl-CH2), 0.81 (t, 6H, Alkyl-CH3);

3JCH2,CH3=6.6 Hz.

4-O-(2',3',4',6'-Tetra-O-acetyl-β-D-glucopyranosyl)-2,3,6-tri-O-acetyl-D-glucopyranoside (Compound 3)

1,2,3,4,2',3',4',6'-Octa-O-acetylmaltose (6.8 g; 10 mmol) was reacted with ammonium carbonate (4.8 g; 50 mmol) in dimethylformamide (50 mL) at ambient temperature for 21 hours. The reaction was filtered and diluted with 200 mL of dichloromethane. The organic phase was washed twice with 100 mL of hydrochloric acid (0.1 m), brine and water. The organic layer was dried over magnesium sulfate and the solvent removed under reduced pressure. The crude product was chromatographed on silica gel (Toluene—ethyl acetate 1:1).

Yield: 4.5 g (71%).

4-O-(2',3',4',6'-Tetra-O-acetyl-β-D-glucopyranosyl)-2,3,6-tri-O-acetyl-α-D-glucopyranosyl trichloracetimidate (Compound 4)

3.2 g (5 mmol) of 3 and 2 mL (2.9 g; 20 mmol) trichloracetonitrile were dissolved in 20 mL of dry dichlormethane under a dry nitrogen atmosphere. 75 µL 1,8-Diazabicyclo[5.4.0]undec-7-en (10% solution in dry dichlormethane) were added dropwise, until the reaction mixture stayed a slightly brown colour. Stirring was continued for an additional hour. The solvent was removed under reduced pressure and the resulting syrup was subjected to chromatographic purification (Ether).

Yield: 3.3 g (85%).

1H-NMR (400 MHz, CDCl3+TMS): δ=8.67 (s, 1H, NH), 6.48 (d, 1H, H-1), 5.45 (d, 1H, H-1'), 5.40 (dd, 1H, H-3'), 5.38 (dd, 1H, H-3), 5.08 (dd, 1H, H-4'), 5.02 (dd, 1H, H-2), 4.88 (dd, 1H, H-2'), 4.51 (dd, 1H, H-6a), 4.28 (dd, 1H, H-6b), 4.23 (dd, 1H, H-6a'), 4.19 (dd, 1H, H-6b'), 4.08 (dd, 1H, H-4), 3.94-4.04 (m, 2H, H-5, H-5'), 2.15, 2.13, 2.10, 2.07, 2.02, 2.01, 1.99 (each s, 3H, OAc);

3J1,2=3.6, 3J2,3=10.2, 3J3,4=9.7, 3J4,5=9.7, 3J5,6a=2.2, 3J5,6b=3.6, 2J6a,b=11.2, 3J1',2'=4.1, 3J2',3'=10.1, 3J3',4'=9.9, 3J5',6a'=4.2, 3J5',6b'=2.8, 2J6a',b'=12.6 Hz.

1,3-Di-O-[cis-9-octadecenyl]-2-O-[4'-O-(2"3",4",6"-Tetra-O-acetyl-α-D-glucopyranosyl)-2',3',6'-tri-O-acetyl-β-D-glucopyranosyl]-sn-glycerol (Compound 5)

781 mg (1 mmol) compound 4, 593 mg (1 mmol) compound 1 and 100 mg of freshly dried powdered molecular sieve (4 Å) were dissolved in 10 mL of anhydrous dichlormethane under an atmosphere of nitrogen. Under cooling (0° C.) 222 mg (1 mmol) Trimethylsilyltrifluormethanesulfonate were added dropwise. Afterwards the reaction mixture was stirred for 6 hours at 0° C. After thin layer chromatography (t.l.c) revealed the reaction to be complete, pyridine was added, 50 mL dichlormethane were added and the reaction mixture was filtered through Celite. The organic phase was washed twice with 10 mL of a saturated solution of sodium hydrogen carbonate and subsequently with 10 mL of water. The organic phase was dried over magnesium sulphate, and solvent was removed under reduced pressure. The residue was purified by short column chromatography (light petroleum b.p. 50-70° C.—ethyl acetate 4:1). Yield: 1.0 g (83%). C65H110O20 (1210.759)

1H-NMR (500 MHz, CDCl3+TMS): δ=5.28-5.43 (m, 4H, H-olefin.), 5.33 (d, 1H, H-1"), 5.29 (dd, 1H, H-3"), 5.17 (dd, 1H, H-3"), 4.98 (dd, 1H, H4"), 4.79 (dd, 1H, H-2"), 4.72 (dd, 1H, H-2'), 4.71 (d, 1H, H-1'), 4.40 (dd, 1H, H-6a'), 4.19 (dd, 1H, H-6a"), 4.15 (dd, 1H, H.6b'), 3.97 (dd, 1H, H-6b"), 3.90 (dd, 1H, H4'), 3.89 (ddd, 1H, H-5"), 3.80-3.87 (m, 1H, H-2), 3.59 (ddd, 1H, H-5'), 3.49 (d, 2H, H-1a, H-3a), 3.29-3.37 (m, 6H, H-1b, H-3b, α-CH2), 2.06, 2.03, 1.97, 1.95 (each s, 3H, OAc), 1.93 (s, 6H, OAc), 1.92 (s, 3H, OAc), 1.86-1.99 (m, 8H, H-allyl.), 1.40-1.53 (m, 4H, β-CH2), 1.12-1.33 (m, 44H, Alkyl-CH2), 0.81 (t, 6H, Alkyl-CH3);

3J1',2'=8.6, 3J2',3'=9.6, 3J3',4'=9.6, 3J4',5'=9.6, 3J5',6a'=2.8, 3J5',6b'=4.5, 3J6a',b'=11.9, 3J1",2"=4.0, 3J2",3"=9.8, 3J3",4"=9.8, 3J4",5"=9.8, 3J5",6a"=4.1, 3J5",6b"=2.0, 3J6a",b"=12.5 Hz.

13C-NMR (125 MHz, CDCl3+TMS): δ=170.55, 170.49, 170.27, 169.98, 169.60, 169.44 (C=O, OAc), 130.08 (C-olefin), 100.86, (C-1'), 96.06 (C-1"), 78.70 (C-2), 75.88 (C-3'), 73.48 (C4'), 72.92 (C-2'), 72.63 (C-5'), 71.86 (α-CH2), 71.31 (C-1, C-3), 70.38 (C-2"), 70.09 (C-3"), 69.25 (C-5"), 68.68 (C-4"), 63.46 (C-6'), 61.77 (C-6"), 33.36 (C-allyl), 32.57, 30.51, 30.26, 30.04, 29.89, 29.79, 29.71, 26.62 (Alkyl-CH2), 20.89, 20.78, 20.68, 20.64, 20.62, 20.60, 20.59 (CH3, OAc), 14.13 (Alkyl-CH3).

1,3-Di-O-[cis-9-octadecenyl]-2-O-[4'-O-(α-D-glucopyranosyl)-β-D-glucopyranosyl]-sn-glycerol (Compound 6)

988 mg (0.815 mmol) compound 5 were deprotected using General procedure 1. The product was purified by gel filtration on a column of Serva LH-20 suspended in methanol.

Yield: 665 mg (89%). C51H96O13 (916.6851)
FAB-MS: m/z=939.7 [M+Na]+
=+22° (c=0.17, MeOH)
1H-NMR (400 MHz, d4-Methanol): δ=5.27-5.38 (m, 4H, H-olefin.), 5.14 (d, 1H, H-1"), 4.31 (d, 1H, H-1'), 3.94-3.97 (m, 1H, H-2), 3.88 (dd, 1H, H6a'), 3.79-3.87 (m, 3H, H-4", H6b', H-6a"), 3.65-3.73 (m, 2H, H-5", H6b"), 3.61 (m, 2H, H-3', H-3"), 3.56 (dd, 1H, H4'), 3.43-3.50 (m, 3H, H-1a, H-3a, H-2"), 3.38 (ddd, 1H, H-5'), 3.24-3.29 (m, 3H, H-1b, H-3b, H-2'), 3.16-3.21 (m, 4H, Alkyl-α-CH2), 1.92-2.05 (m, 8H, —CH2-allyl.), 1.48-1.57 (m, 4H, Alkyl-α-CH2), 1.16-1.41 (m, 44H, Alkyl-CH2), 0.88 (t, 3H, Alkyl-CH3);

3J1',2'=8.1, 3J3',4'=9.2, 3J4',5'=9.3, 3J5',6a'=2.1, 3J5', 6b'=5.6, 2J6a',b'=12.2, 3J1",2"=3.6 Hz.

1,3-Di-O-tetradecyl-2-O-[4'-O-(2",3",4",6"-tetra-O-acetyl-α-D-glucopyranosyl)-2',3',4'-tri-O-acetyl-β-D-glucopyranosyl]-sn-glycerol (Compound 7)

3.39 g (5 mmol) Maltoseperacetate and 2.42 g (5 mmol) compound 2 were dissolved in 50 mL of dry dichlormethane under an atmosphere of dry nitrogen. 994 mg (880 μL; 7 mmol) boron trifluoride etherate were added and the solution was stirred for 6 hours at ambient temperature until t.l.c. revealed the reaction to be complete. The reaction was quenched with 50 mL of a saturated solution of sodium hydrogen carbonate, the organic layer was separated and the aqueous layer extracted twice with dichlormethane. The combined organic phases were washed twice with water, dried over magnesium sulphate and evaporated in vacuo. The residue was purified by column chromatography (light petroleum b.p. 50-70° C.—ethyl acetate 2:1).

Yield: 3.00 g (54%). C57H98O20 (1102.6651)
1H-NMR (400 MHz, CDCl3+TMS): δ=5.34 (d, 1H, H-1"), 5.29 (dd, 1H, H-3"), 5.18 (t, 1H, H-3'), 4.98 (t, 1H, H4"), 4.79 (dd, 1H, H-2"), 4.74 (dd, 1H, H-2'), 4.70 (d, 1H, H-1'), 4.40 (dd, 1H, H-6a'), 4.19 (dd, 1H, H-6a"), 4.15 (dd, 1H, H-6b'), 3.97 (dd, 1H, H-6b"), 3.91 (t, 1H, H-4'), 3.80-3.91 (m, 2H, H-2, H-5"), 3.59 (ddd, 1H, H-5'), 3.44-3.51 (m, 2H, H-1a, H-3a), 3.29-3.38 (m, 6H, H-1b, H-3b, Alkyl-α-CH2), 2.07, 2.03, 1.98, 1.96 (each s, 3H, OAc), 1.93 (s, 6H, OAc), 1.92 (s, 3H, OAc), 1.42-1.52 (m, 4H, α-CH2), 1.16-1.25 (m, 44H, Alkyl-CH2), 0.81 (t, 6H, Alkyl-CH3);

3J1',2'=8.1, 3J2',3'=9.7, 3J3',4'=9.7, 3J4',5'=9.7, 3J5', 6a'=2.8, 3J5', 6b'=4.8, 2J6a',6b'=12.2, 3J1",2"=3.8, 3J2", 3"=9.7, 3J3",4"=9.7, 3J4",5"=9.7, 3J5", 6a"=4.1, 3J5", 6b"=2.3, 2J6a",6b"=12.9, 3JCH2,CH3=6.6 Hz.

13C-NMR (100 MHz, CDCl3+TMS): δ=170.94, 170.87, 170.62, 170.34, 170.05, 169.82 (C=O, OAC), 100.66 (C-1"), 95.94 (C-1'), 78.75 (C-2), 75.94 (C-3'), 73.25 (C-4'), 72.81 (C-2'), 72.43 (C-5'), 72.19, 72.10 (C-α), 71.66, 70.92 (C-1, C-3), 70.40 (C-2"), 70.09 (C-3"), 69.80 (C-5"), 68.47 (C4–), 63.33 (C-6'), 61.94 (C-6"), 32.34, 30.12, 30.08, 29.95, 29.78, 26.56, 26.53, 23.11 (Alkyl-CH2), 21.35, 21.25, 21.11, 21.06, 21.00 (—CH3, OAc), 14.54 (Alkyl-CH3).

1,3-Di-O-tetradecyl-2-O-[4'-O-(α-D-glucopyranosyl)-β-D-glucopyranosyl]-sn-glycerol (Compound 8)

2.98 g (2.70 mmol) compound 7 were deprotected using general procedure 1. The product was recrystallised from methanol.

Yield: 2.10 g (90%). C43H84O13 (808.5912)
MALDITOF-MS: m/z=831.6 [M+Na]+
=+20° (c=1.0, MeOH)
1H-NMR (500 MHz, d4-Methanol): δ=5.19 (d, 1H, H-1"), 4.30 (d, 1H, H-1'), 3.94-3.96 (m, 1H, H-2), 3.89 (dd, 1H, H-6a'), 3.76-3.87 (m, 3H, H4", H-6b', H-6a"), 3.66-3.73 (m, 2H, H-5", H-6b"), 3.58-3.63 (m, 2H, H-3', H-3"), 3.52 (dd, 1H, H-4'), 3.43-3.50 (m, 3H, H-1a, H-3a, H-2"), 3.39 (ddd, 1H, H-5'), 3.22-3.29 (m, 3H, H-1b, H-3b, H-2'), 3.17-3.21 (m, 4H, Alkyl-α-CH2), 1.41-1.50 (m, 4H, Alkyl-α-CH2), 1.16-1.35 (m, 44H, Alkyl-CH2), 0.88 (t, 6H, Alkyl-CH3);

3J1',2'=8.1, 3J3',4'=9.1, 3J4',5'=9.1, 3J5',6a'=2.1, 3J5', 6b'=5.7, 2J6a','=12.1, 3J1",2"=3.6 Hz.

1,3-di-O-tetradecyl-2-O-[6'-O-(2",3",4",6"-tetra-O-acetyl-α-D-galactopyranosyl)-2',3',4'-tri-O-acetyl-β-D-glucopyranosyl]-sn-glycerol (Compound 9)

The reaction was carried out as described for compound 7 using 2.95 g (4.3 mmol) Melibioseperacetate, 2.3 g (4.3 mmol) 2 and 854 mg (760 μL; 6 mmol) boron trifluoride etherate. The product was purified using light petroleum b.p. 50-70° C.—ethyl acetate 2:1 as eluent.

Yield: 2.05 g (43%). C57H98O20 (1102.6651)
1H-NMR (500 MHz, CDCl3+TMS): δ=5.39 (dd, 1H, H-4"), 5.27 (dd, 1H, H-3"), 5.13 (t, 1H, H-3'), 5.09 (d, 1H, H-1"), 5.05 (dd, 1H, H-2"), 5.04 (dd, 1H, H4'), 4.83 (dd, 1H, H-2'), 4.71 (d, 1H, H-1'), 4.15 (mc, 1H, H-5'), 4.00-4.08 (m, 2H, H-6a", H-6b"), 3.82-3.87 (m, 1H, H-2), 3.68 (dd, 1H, H-6a'), 3.45-3.57 (m, 4H, H-1a, H-3a, H-5', H-6b'), 3.29-3.37 (m, 6H, H-1b, H-3b, alkyl-α-CH2), 2.06, 1.98, 1.97, 1.96, 1.93, 1.91 (each s, 3H, OAc), 1.43-1.51 (m, 4H, alkyl-α-CH2), 1.14-1.28 (m, 44H, alkyl-CH2), 0.81 (t, 6H, alkyl-CH3);

3J1',2'=7.9, 3J2',3'=9.5, 3J3',4'=9.5, 3J4',5'=9.7, 3J5'6a'=4.1, 2J6a',b'=11.0, 3J1",2"=3.8, 3J2",3"=10.7, 3J3", 4"=3.5, 3J4",5"=1.0, 3JCH2, CH3=6.9 Hz.

13C-NMR (125 MHz, CDCl3+TMS): δ=170.95, 170.77, 170.74, 170.58, 170.16, 169.76, 169.70 (C=O, OAc), 100.94 (C-1'), 97.13 (C-1"), 78.39 (C-2), 73.00 (C-3'), 72.17 (C-5'), 72.10, 71.92 (C-α), 71.38 (C-2'), 71.70, 70.97 (C-1, C-3), 69.37 (C-4'), 68.36, 68.31 (C4", C-2"), 67.85 (C-3"), 66.85 (C-5"), 66.83 (C-6'), 62.10 (C-6"), 32.33, 30.12, 30.08, 29.96, 29.78, 26.58, 26.54, 23.10 (Alkyl-CH2), 21.23, 21.12, 21.04, 20.80 (—CH3, OAc), 14.53 (Alkyl-CH3).

1,3-di-O-tetradecyl-2-O-[6'-O-(α-D-galactopyranosyl)-α-D-glucopyranosyl]-sn-glycerol (Compound 10)

1.95 g (1.77 mmol) compound 9 were deprotected using general procedure 1. The product was recrystallised from 2-propanol.

Yield: 1.27 g (89%). C43H84O13 (808.5912)
MALDITOF-MS: m/z=831.5 [M+Na]+
=+23° (c=0.8, CH3COCH3)
1H-NMR (400 MHz, d4-Methanol): δ=4.89 (d, 1H, H-1"), 4.31 (d, 1H, H-1'), 4.01 (dd, 1H, H-6a'), 3.90-3.95 (m, 2H, H-4", H-5", H-2), 3.69-3.80 (m, 5H, H-2", H-3", H-6a", H-6b', H-6b"), 3.50 (ddd, 1H, H-5'), 3.43-3.49 (m, 3H, H-1a, H-3a, H-4'), 3.38 (dd, 1H, H-3'), 3.20-3.28 (m, 3H, H-1b, H-3b, H-2'), 3.17-3.22 (m, 4H, Alkyl-α-CH2), 1.40-1.49 (m, 4H, β-CH2), 1.16-1.36 (m, 44H, Alkyl-CH2), 0.88 (t, 6H, Alkyl-CH3);
3J1',2'=8.1, 3J2',3'=9.2, 3J3',4'=9.2, 3J4',5'=9.2, 3J5',6b'=2.0, 3J1",2"=4.1 Hz.

Glycolipid 1: 1,3-Di-O[cis-9-octadecenyl]-2-O-[4'-O-(α-D-glycopyranosyl)-β-D-glycopyranosyl]-sn-glycerol 988 mg (0.815 mmol) compound 8 were deprotected using General procedure 1. The product was purified by gel filtration on a column of Serva LH-20 suspended in methanol.

Yield: 665 mg (89%). C51H96O13 (916.6851)
FAB-HIRESMS: m/z=939,6712 [M+Na]+(calc. 939.6749)
$[\alpha]_D^{20}$=+22° (c=0.17, MeOH)

Glycolipid 5: 1,3-Di-O-tetradecyl-2-O-[4'-O-(α-D-glucopyranosyl)-β-D-glucopyranosyl]-sn-glycerol 2.98 g (2.70 mmol) compound 7 were deprotected using general procedure 1. The product was recrystallised from methanol.

Yield: 2.10 g (90%). $C_{43}H_{84}O_{13}$ (808.5912)
MALDITOF-MS: m/z=831.6 [M+Na]+
$[\alpha]_D^{20}$=+20° (c=1.0, MeOH)
$^1$H-NMR (500 MHz, d$_4$-Methanol): δ=5.19 (d, 1H, H-1"), 4.30 (d, 1H, H-1'), 3.94-3.96 (m, 1H, H-2), 3.89 (dd, 1H, H-6a'), 3.76-3.87 (m, 3H, H-4", H-6b', H-6a"), 3.66-3.73 (m, 2H, H-5", H-6b"), 3.58-3.63 (m, 2H, H-3', H-3"), 3.52 (dd, 1H, H-4'), 3.43-3.50 (m, 3H, H-1a, H-3a, H-2"), 3.39 (ddd, 1H, H-5'), 3.22-3.29 (m, 3H, H-1b, H-3b, H-2'), 3.17-3.21 (m, 4H, Alkyl-α-CH$_2$), 1.41-1.50 (m, 4H, Alkyl-β-CH$_2$), 1.16-1.35 (m, 44H, Alkyl-CH$_2$), 0.88 (t, 6H, Alkyl-CH$_3$);
$^3J_{1',2'}$=8.1, $^3J_{3',4'}$=9.1, $^3J_{4',5'}$=9.1, $^3J_{5',6a'}$=2.1, $^3J_{5',6b'}$=5.7, $^2J_{6a',b'}$=12.1, $^3J_{1",2"}$=3.6 Hz.

Glycolipid 6: 1,3-di-O-tetradecyl-2-O-[6'-O-(α-D-galactopyranosyl)-β-D-glucopyranosyl]-sn-glycerol 1.95 g (1.77 mmol) compound 9 were deprotected using general procedure 1. The product was recrystallised from 2-propanol.

Yield: 1.27 g (89%). $C_{43}H_{84}O_{13}$ (808.5912)
MALDITOF-MS: m/z=831.5 [M+Na]+
$[\alpha]_D^{20}$=+23° (c=0.8, CH$_3$COCH$_3$)
$^1$H-NMR (400 MHz, d$_4$-Methanol): δ=4.89 (d, 1H, H-1"), 4.31 (d, 1H, H-1'), 4.01 (dd, 1H, H-6a'), 3.90-3.95 (m, 2H, H-4", H-5", H-2), 3.69-3.80 (m, 5H, H-2", H-3", H-6a", H-6b', H-6b"), 3.50 (ddd, 1H, H-5'), 3.43-3.49 (m, 3H, H-1a, H-3a, H-4'), 3.88 (dd, 1H, H-3'), 3.20-3.28 (m, 3H, H-1b, H-3b, H-2'), 3.17-3.22 (m, 4H, Alkyl-α-CH$_2$), 1.40-1.49 (m, 4H, β-CH$_2$), 1.16-1.36 (m, 44H, Alkyl-CH$_2$), 0.88 (t, 6H, Alkyl-CH$_3$);
$^3J_{1',2'}$=8.1, $^3J_{2',3'}$=9.2, $^3J_{3',4'}$=9.2, $^3J_{4',5'}$=9.2, $^3J_{5',6a'}$=4.1, $^3J_{5',6b'}$=2.0, $^3J_{1",2"}$=4.1 Hz.

2. Intranasal and Intraperitoneal Co-Administration of Glycolipids 1, 5 or 6, Respectively, with a Soluble Antigen Stimulates Efficient Humoral Responses Experimental protocol: six-eight weeks-old female BALB/c (H-2d) mice were purchased from Harlan Winkelmann GmbH (Borchen, Germany) and treated in accordance with local and European Community guidelines. Groups of 5 mice each were immunized on day 01, 14 and 28 with 30 μg of β-Gal (Boehringer, Mannheim, Germany), alone or with 10 μg of glycolipids 1, 5, or 6, respectively, see FIG. 2. For intranasal (i.n.) immunization, 10 μl were applied to each naris, whereas for the s.c. injection β-Gal with or without glycolipids 1, 5 or 6, respectively, was resuspended in a volume of 50 μl PBS per animal. Serum samples were collected at day 38 after immunization and stored at −20° C. prior to determination of β-Gal-specific antibodies. 96-well Nunc-Immuno MaxiSorp assay plates (Nunc, Roskilde, Denmark) were coated with 100 μl of β-Gal (Boehringer, Mannheim, Germany) at 5 μg/ml in 0.05 M carbonate buffer (pH 8.2) per well. Serial two-fold dilutions of sera or lavages in PBS with 1% BSA and 0.05% Tween 20 were added (100 μl/well), and plates incubated for 16 h at 37° C. After washing, biotinylated γ-chain-specific goat anti-mouse IgG (Sigma Chemie, Deisenhofen, Germany) was added, and plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. Endpoint titers were expressed as the reciprocal log 2 of the last dilution, which gave an optical density at 405 nm of 0.1 units above the values of the negative controls after 15 to 30 min of incubation.

In view of the above in vitro results, additional in vivo studies have been conducted. In detail, the immune responses using glycolipids 1, 5 or 6, respectively, as adjuvant applied by the two most effective routes, namely s.c. and i.n. were determined. Thus, the capacity of glycolipids 1, 5 or 6, respectively, to stimulate efficient humoral immune responses was evaluated, by determining the serum titers of β-Gal-specific antibodies in vaccinated mice.

Figure 2:
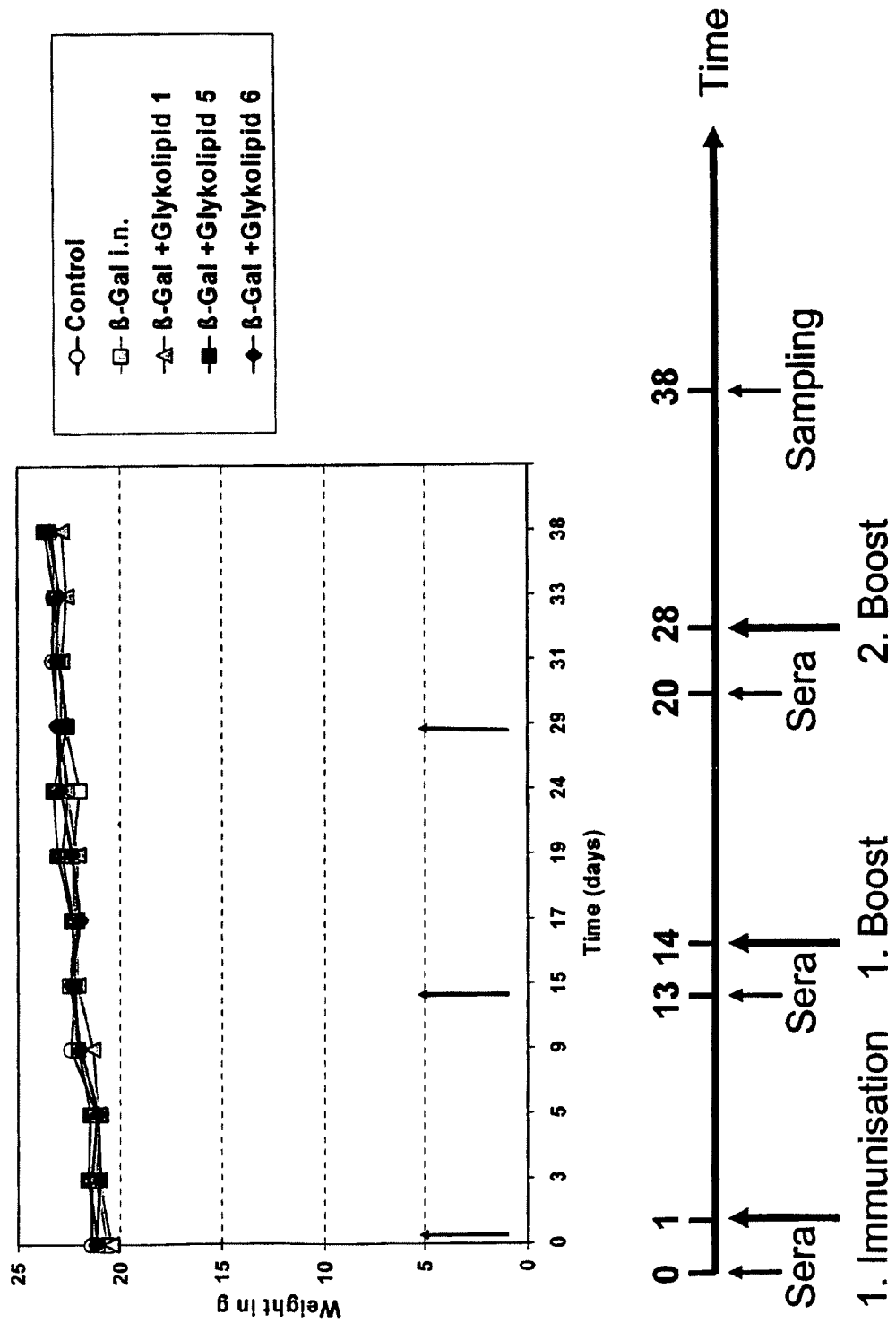
FIG. 2.
Co-administration of 30 µg β-Gal (in the following, β-Gal will be used always in an amount of 30 µg unless otherwise indicated) with the new adjuvants glycolipid 1, 5 and 6 induced antigen-specific immune response and showed no toxic side effects by intranasal (i.n.) and subcutaneous (s.c.) immunisation routes (parenteral route not shown) in Balb/c mice. The body weight and the behaviour of the animals were tested daily. The Balb/c mice were immunized by the mucosal (i.n.) or parenteral (s.c.) route with β-Gal alone or together with glycolipids 1, 5 and 6 three times at 2-wk intervals (day 1, 14 and 28). 10 days after the final immunization (day 38), the immunized mice were sacrificed.

The co-administration of the glycolipids 1, 5, and 6, respectively, were well tolerized and the immunized animals showed no toxic side effects or changes in their behaviour, as shown by the development of weight (FIG. 2).

As shown in FIG. 3, i.n. administration of β-Gal alone (30 μg/dose) resulted in the induction of very low antibody titers, even after the second boost (FIG. 3A). In contrast, in the presence of glycolipids 1, 5 or 6, respectively, i.n. administration of β-Gal induced very high titers of specific IgG in all mice, in particular glycolipids 1 and 5 elicited high specific IgG titer. Vaccination by the parenteral route results in IgG titers of about 2 fold higher in comparison to vaccination using β-Gal alone. The increase of the dosage to 20 or 30 μg glycolipid per animal resulted in an increase of the immune response in a dose dependent manner (FIG. 4A).

A significant adjuvanticity was also observed when glycolipids 1, 5 or 6, respectively, were administered by the s.c. route (FIG. 3B and FIG. 4B). Animals immunized with β-Gal co-administered with glycolipids 1, 5 or 6, respectively, resulted in increased β-Gal-specific IgG titers in comparison to animals immunized with β-Gal alone (FIG. 3B). Dose dependent increase of the immune response was observed also when immunised by the s.c. route (FIG. 3B and FIG. 4B)

3. Intranasal Co-Administration of Glycolipids 1, 5 or 6, Respectively, with a Soluble Antigen Stimulate Efficient Mucosal Antibody Responses Experimental protocol: at day 38, mice were sacrificed and the final sampling was performed. Vaginal and lung lavages were obtained by flushing the organs with 1 ml of PBS supplemented with 50 mM EDTA, 0.1% BSA, and 10 mM PMSF. Lavages were then centrifuged to remove debris (10 min at 3000×g), and supernatant fluids were stored at −20° C. To determine the concentration of total IgA present in the lung and vaginal lavages, serial dilutions of the corresponding samples were incubated in microtiter plates that were previously coated with goat anti-mouse IgA (Sigma Chemie), as capture antibodies (100 μl/well). Serial dilutions of purified mouse IgA (Sigma Chemie) were used to generate a standard curve.

To investigate the capacity of glycolipids 1, 5 or 6, respectively, to stimulate mucosal responses against antigens co-administered by the i.n. route, the production of β-Gal-specific IgA in lung was analyzed (FIG. 4A) from immunized animals, immunized according to the protocol described in Example 2. While i.n. immunization with β-Gal alone resulted in a weak production of detectable levels of β-Gal-specific IgA in lung lavages, a significant increase in the levels of antigen-specific IgA was detected in animals immunized with β-Gal and glycolipid 5 (10 μg) (FIG. 5A) and glycolipids 5 or 6, respectively (20 μg and 30 μg, FIG. 6A).

In addition, moderate responses were detected in the genital tract in a dose dependent manner (FIGS. 5B and 6B). In contrast, β-Gal specific IgA were below the detection level in mice receiving β-Gal alone or admixed with glycolipids 1 or 6 in lower concentrations (FIG. 6A) and in vaginal lavages (FIGS. 6B and 7B).

To conclude, i.n. vaccination with β-Gal protein in combination with glycolipids 5 and 6 promotes strong humoral immune responses characterized by high titers of β-Gal specific antibodies both in serum and in mucosal lavages (FIG. 3 to 6). The mucosal as the parenteral immunization approach with glycolipids 5 and 6 induced both systemic and mucosal responses. In particular, following the first immunization, serum IgG were induced whereas two mucosal boostings with β-Gal and glycolipids 5 and 6, respectively, by the i.n. route were sufficient to consistently increase the levels of antigen specific secretory IgA in mucosal lavages. However, sIgA and to a lesser extent serum IgG titers were enhanced in animals which observed the higher concentration of the glycolipids 5 and 6, respectively.

4. Glycolipids 1, 5 and 6 Stimulate Efficient T Cell-Mediated Proliferative Responses When Co-Administered with Soluble Antigens Experimental protocol: Spleens were removed and pooled for analysis of cellular immune responses. Cells were grown in RPMI 1640 supplemented with 10% fetal calf serum, 100 U/ml of penicillin, 50 μg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Spleen cell suspensions were adjusted to $5 \times 10^6$ cells/ml in complete medium, cells were seeded with 100 μl per well in a flat-bottomed 96-well microtiter plate (Nunc) and plates were incubated for 4 days. Unstimulated spleen cells were incubated in the presence of different concentrations of the new adjuvants to analyze the in vitro stimulation capacity of glycolipids 1, 5 or 6, respectively. T cellmediated immune responses were investigated at day 38 by measuring the proliferation of cells recovered from spleens after in vitro restimulation with β-Gal. Said spleen cells were obtained from vaccinated mice—said mice where immunized as described in Example 2—and incubated in the presence of different concentrations of the soluble β-Gal antigen. Each concentration was tested in triplicates. During the final 18 h of culture, 1 μCi of [$^3$H]thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [$^3$H] thymidine into the DNA of proliferating cells was determined by a β-scintillation counter (Wallac 1450, Micro-Trilux). The results are expressed as the arithmetic mean of [$^3$H]thymidine uptake in cpm.

Thirty eight days following vaccination, spleens cells were recovered and purified, re-stimulated in vitro in the presence of various amounts of β-Galactosidase and their proliferative capacity was estimated by measuring the incorporation of [$^3$H]thymidine into their DNA using a β-scintillation counter. Spleen cells from animals immunized by s.c. injection of β-Gal alone, which were chosen as a control, exhibited a significant proliferative response as compared to the non immunized group (FIGS. 7B and 8B). A further increase in proliferation was noted in spleen cells from animals co-administrated with glycolipids 1, 5 or 6, respectively, and antigen. While i.n. administration of β-Gal alone failed to induce detectable cellular proliferation, co-administration of glycolipid 5 triggered the induction of an efficient proliferative response at yet low amounts of antigen (see FIG. 7A). At higher levels of the antigens glycolipids 5 and 6, respectively, strong responses were observed in mize immunized with the β-Gal protein and the antigen (FIG. 8A). Thus, strong proliferative responses were induced in spleen.

Of note, the T cell proliferative response was observed with spleen cells of mice immunized with glycolipids 5 or 6, respectively, and β-Gal administered by the i.n. and the s.c. route, respectively (see FIGS. 7A and B and 8A and B).

In all cases a dosis dependent effect was observed when increasing the concentration of β-Gal in the re-stimulation experiment. Thus, the use of the new adjuvants glycolipids 1, 5 or 6, respectively, resulted in a statistically significant increment of the T cell proliferation after i.n. and s.c. administration. These results demonstrate that glycolipids 1, 5 or 6, respectively, can increase the cellular immune response.

5. Analysis of the T Helper Patterns Stimulated by Using Glycolipids 1, 5 or 6, Respectively, as Adjuvant Experimental Protocol:

Isotyp ELISA: 96-well Nunc-Immuno MaxiSorp assay plates (Nunc, Roskilde, Denmark) were coated with 100 μl of β-Gal (Boehringer, Mannheim, Germany) at 5 μg/ml in 0.05 M carbonate buffer (pH 8.2) per well. Serial two-fold dilutions of sera or lavages in PBS with 1% BSA and 0.05% Tween 20 were added (100 μl/well), and plates incubated for 2 h at 37° C. After washing, biotin-conjugated rat anti-mouse IgG1 or IgG2a (Pharmingen, Hamburg, Germany) were added to determine IgG subclasses. Plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. To determine the concentration of IgG subclasses in serum, standard curves were obtained by coating the wells with an isotype-specific goat anti-mouse IgG, and then by incubating with purified mouse IgG1 or IgG2a antibodies (Dianova, Hamburg, Germany).

The pattern of the different subclasses of the β-Gal antigen-specific IgG isotypes present in the sera of vaccinated mice is shown in FIG. 9. FIG. 9 shows on the left side the results for intranasal administration of β-Gal alone, β-Gal and glycolipids 1, 5 or 6, respectively. The protocol for vaccination was identical to the protocol described in Example 2. As can be ascertained from FIG. 9, the amount of antigen specific antibodies of the IgG1 and IgG2a subtypes were strongly increased (significant enhancement of β-Gal specific IgG1 (50-fold) and IgG2a (6-fold) secretion, $p \leq 0.016$ and $p \leq 0.095$, respectively) after intranasal administration of the antigen using glycolipid 5 as mucosal adjuvant. Animals immunized with glycolipid 6 by the i.n. route showed an 24-fold increase in IgG1 secretion and a 1.8-fold increase in IgG2a secretion in comparison to animals which were immunized with β-Gal alone, whereas glycolipid 1 showed no effect. Further, in case of systemic administration, here subcutaneous administration, of β-Gal co-administered with glycolipid 1 or glycolipid 5, a significant enhancement (2.5-fold and 2.2-fold increase, respectively, $p \leq 0.032$ and $p \leq 0.056$, respectively) of the expression of antigen specific IgG1 isotypes were observed, whereas glycolipid 6 had no effect. Furthermore, there was no enhanced secretion of IgG2a isotype observed. The data represents the average titer of a group of 5 animals.

The subclass distribution of β-Gal specific serum IgG was analyzed sin d the IgG1 and IgG2a isotypes are considered to result from stimulation by Th2 and Th1 cells, respectively. As shown in FIG. 9 and FIG. 10, i.n. co-administration of βGal protein and glycolipid 6 led to similar levels of IgG1 and IgG2a. In contrast, s.c. immunisation induced a dominant Th2 response with increased IgG1 isotype expression. Glycolipids 1 and 5 induced a dominant Th2 pattern with increased IgG1 isotype expression after i.n. and s.c administration.

To characterize the type of Th response stimulated following immunization, the content of IFN-γ, IL-2, IL-4, IL-5, and TNFα was measured in supernatants from in vitro re-stimulated spleen cells (FIGS. 8 and 9) by the Cytometric Bead Array. Culture supernatants from proliferating cells were collected on days 2 and 4, and stored at −70° C. Determinations of IFN-γ, TNFα, IL-2, IL-4, and IL-5 were performed by cytometric bead array analysis using the commercial kit from BectonDickinson, according to the manufacturer's instructions. A standard curve was generated for each cytokine by using the corresponding recombinant murine cytokines (Pharmingen). Probes were incubated at room temperature for additional 2 h. The probes were analyzed subsequently by flow cytometry as described in the protocol of BD.

The spleen cells of mice immunized with β-Gal co-administered with glycolipid 5 by the intranasal route showed enhanced expression of proinflammatory (TNFα), Th1 (IFNγ and IL-2) and Th2 (IL-5) cytokines in response to enhanced concentrations of the β-Gal antigen, shown by the enhanced stimulation index (B). Curves represent cytokine concentration (pg/ml) and Stimulation index (SI) in response to enhanced antigen concentration in each group. Each group consists of five mice. Data are representative of two separate experiments.

6. Analysis of the T Helper Patterns Stimulated by Using Glycolipids 1, 5 or 6, Respectively, as Adjuvant by Elispot Experimental protocol: Spleens from vaccinated mice were removed and pooled for analysis of cellular immune responses. The protocol for vaccination was identical to the protocol described in Example 2. Cells were grown in RPMI 1640 supplemented with 10% fetal calf serum, 100 U/ml of penicillin, 50 μg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 μl per well in a flat-bottomed 96-well microtiter plate (Nunc) and plates were incubated for 4 days in the presence of different concentrations of soluble β-Gal.

Splenocytes of mice immunized by the i.n. (FIG. 12) and s.c. (FIG. 13) route were collected and cultured with different concentrations of the antigen. A total of $5 \times 10^6$ cells/ml spleen cells were cultured with 2 μg/ml of the MHC cI.I restricted β-Gal peptide (IFNγ) for 24 h and the β-Gal-Protein (IL-2 and 4) for 48 h. IFNγ producing CD8+ T cells were analyzed using BD Elispot kit according to the manufacturer's instructions. The spleen cells of mice immunized with β-Gal co-administered with glycolipid 5 by the intranasal route showed enhanced expression of spot forming units (SFU) secreting IFNγ in response to the antigen, whereas the co-administration of glycolipids 1 and 6 showed only a weak secretion of IFNγ. The parenteral administration of with β-Gal admixed with glycolipids 1, 5 and 6 showed only weak enhanced secretion of IFNγ, IL-2 and IL-4 in response to the β-Gal antigen in comparison to animals which were immunized with β-Gal alone. Bars represent Spot forming units of $10^6$ splenocytes with subtracted background mean SFU±SE in each group. Each group consists of five mice. Data are representative of three separate experiments.

Co-administration of β-Gal with 20 up to 30 μg glycolipids 5 and 6 induced a strong cellular immune responses and enhanced levels of IFNγ, IL-2 and IL-4 in response to enhanced concentration of the β-Gal antigen in Balb/c mice. Balb/c mice were immunized by the i.n. or s.c. route with β-Gal alone or together with glycolipids 5 and 6 three times at 2-wk intervals. 10 days after the final immunization, the immunized mice were sacrificed. Splenocytes of mice immunized by the i.n. (FIG. 14) and s.c. (FIG. 15) route were collected and cultured with different concentrations of. A total of $5 \times 10^6$ cells/ml spleen cells were cultured with 2 μg/ml of the MHC cI.I restricted β-Gal peptide (IFNγ) for 24 h and the β-Gal-Protein (IL-2 and 4) for 48 h. IFNγ producing CD8+ T cells were analyzed using BD Elispot kit according to the manufacturer's instructions. The spleen cells of mice immunized with β-Gal co-administered with glycolipid 5 by the intranasal route showed enhanced expression of spot forming units (SFU) secreting IFNγ in a dose dependent matter in response to the antigen, whereas the co-administration of glycolipid 6 showed a reduced cytokine secretion in response to the β-Gal antigen. The parenteral administration of with β-Gal co-administered with glycolipids 5 and 6 showed only a minor effect in the secretion of IFNγ, IL-2 and IL-4 in response to the β-Gal antigen in comparison to control animals. Bars represent Spot forming units of 106 splenocytes with subtracted background mean SFU±SEM in each group. Each group consists of five mice. Data are representative of three separate experiments.

The invention claimed is:

1. A method of administering an adjuvant to a subject in need thereof, comprising the step of providing to said subject a glycolipid of the general formula (I):

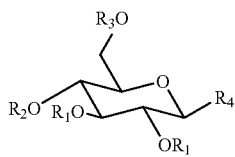

(I)

wherein
$R_1$ is independently selected from the group of hydrogen, and substituted or unsubstituted $C_1$ to $C_6$ alkyl- or $C_1$ to $C_6$ acyl-group;
one of $R_2$, and $R_3$ is hydrogen where
  $R_2$ is a substituted or unsubstituted α-D-glycopyranosyl, α-D-galactopyranosyl, 4'-O-(α-D-glycopyranosyl)-α-D-glycopyranosyl, 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl when $R_3$ is hydrogen;
  $R_3$ is a substituted or unsubstituted α-D-glycopyranosyl, α-D-galactopyranosyl, 4'-O-(α-D-glycopyranosyl)-α-D-glycopyranosyl, 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl when $R_2$ is hydrogen;
$R_4$ is

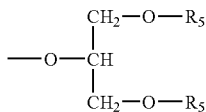

wherein $R_5$ is independently any one of a substituted or unsubstituted $C_5$ to $C_{30}$ alkyl- or alkenyl or salts or solvates thereof,
wherein said glycolipid is provided in a form suitable for mucosal administration.

2. The method use according to claim 1 wherein said glycolipid is administered by a route selected from intranasal, intra NALT, oral, intra-rectal, intrapulmonary, intra-bronchial, intra-tecal, conjunctival, intra-vaginal or intra-urethral administration, and administration into the ducts of the breast or by inhalation.

3. The method according to claim 1 wherein $R_2$ is a substituted or unsubstituted α-D-glycopyranosyl, α-D-galactopyranosyl, 4'-O-(α-D-glycopyranosyl)-α-D-glycopyranosyl 4'-O-(α-D-glycopyranosyl)-α-D-galactopyranosyl, 4'-O-(α-D-galactopyranosyl)-α-D-galactopyranosyl, or 4'-O-(α-D-galactopyranosyl)-α-D-glycopyranosyl and $R_3$ is hydrogen.

4. The method according to claim 1 wherein $R_1$ is hydrogen.

5. The method according to claim 1 wherein $R_4$ is

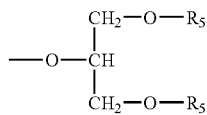

wherein $R_5$ is independently a methyl branched $C_{12}$ to $C_{20}$ alkyl group, a $C_{12}$ to $C_{20}$ alkyl group or a $C_{12}$ to $C_{20}$ alkenyl group.

6. The method according to claim 5 wherein $R_5$ is independently a cis-9-octadecenyloxy-group or a tetradecyl group.

7. The method according to claim 1 wherein the glycolipid is 1,3-di-O-(tetradecyl)-2-O-[4'-O-(α-D-glycopyranosyl)-β-D-glycopyranosyl]sn glycerol.

8. The method according to claim 1 wherein the glycolipid is 1,3-di-O-(cis-9-octadecenyl)-2-O-[4'-O-(α-D-glycopyranosyl)-β-D-glycopyranosy]sn glycerol.

9. The method according to claim 1, wherein the glycolipid is methyl branched 1,3-di-O-(tetradecyl)-2-O-[4'-O-(α-D-galactopyranosyl)-β-D-glycopyranosy]sn glycerol.

* * * * *